US011603566B2

(12) United States Patent
Goel et al.

(10) Patent No.: US 11,603,566 B2
(45) Date of Patent: Mar. 14, 2023

(54) METHODS FOR DIAGNOSING AND TREATING ESOPHAGEAL CANCER

(71) Applicant: BAYLOR RESEARCH INSTITUTE, Dallas, TX (US)

(72) Inventors: Ajay Goel, Dallas, TX (US); Jinsei Miyoshi, Dallas, TX (US)

(73) Assignee: Cancer Diagnostics Research Innovation, Colleyville, TX (US)

( * ) Notice: Subject to any disclaimer, the term of this patent is extended or adjusted under 35 U.S.C. 154(b) by 393 days.

(21) Appl. No.: 16/322,380

(22) PCT Filed: Aug. 4, 2017

(86) PCT No.: PCT/IB2017/054800
§ 371 (c)(1),
(2) Date: Jan. 31, 2019

(87) PCT Pub. No.: WO2018/025242
PCT Pub. Date: Feb. 8, 2018

(65) Prior Publication Data
US 2019/0185944 A1 Jun. 20, 2019

Related U.S. Application Data

(60) Provisional application No. 62/371,028, filed on Aug. 4, 2016.

(51) Int. Cl.
C12Q 1/68 (2018.01)
C12Q 1/6886 (2018.01)
A61P 35/04 (2006.01)
A61K 33/243 (2019.01)
A61K 31/337 (2006.01)
A61K 31/351 (2006.01)
A61K 31/513 (2006.01)
C12Q 1/02 (2006.01)

(52) U.S. Cl.
CPC .......... *C12Q 1/6886* (2013.01); *A61K 31/337* (2013.01); *A61K 31/351* (2013.01); *A61K 31/513* (2013.01); *A61K 33/243* (2019.01); *A61P 35/04* (2018.01); *C12Q 1/025* (2013.01); *C12Q 2600/158* (2013.01); *C12Q 2600/178* (2013.01)

(58) Field of Classification Search
None
See application file for complete search history.

(56) References Cited

U.S. PATENT DOCUMENTS 5,143,854 A 9/1992 Pirrung et al.
5,384,261 A 1/1995 Winkler et al.
5,424,186 A 6/1995 Fodor et al.
5,445,934 A 8/1995 Fodor et al.
5,677,195 A 10/1997 Winkler et al.
5,708,153 A 1/1998 Dower et al.
5,744,305 A 4/1998 Fodor et al.
5,770,358 A 6/1998 Dower et al.
5,789,162 A 8/1998 Dower et al.
5,800,992 A 9/1998 Fodor et al.
6,040,193 A 3/2000 Winkler et al.
6,050,193 A 4/2000 DeBoer et al.
2010/0285471 A1* 11/2010 Croce .................... A61P 35/00
435/6.14

FOREIGN PATENT DOCUMENTS

CN 105176983 12/2015
WO WO 2008/064519 6/2008
WO WO-2008064519 A1 * 6/2008 .......... C12N 15/113

OTHER PUBLICATIONS

Komatsu et al (British Journal of Cancer (2014) 111, 1614-1624 | doi: 10.1038/bjc.2014.451) (Year: 2014).*
MiRBase MI0000269 change log. Obtained from https://www.mirbase.org/cgi-bin/mirna_history.pl?acc=MI0000269 on May 19, 2022. 1 page. (Year: 2022).*
MiRBase MI0000809 change log. Obtained from https://www.mirbase.org/cgi-bin/mirna_history.pl?acc=MI0000809 on May 19, 2022. 1 page. (Year: 2022).*
Napier et al. (World J Gastrointest Oncol May 15, 2014; 6(5): 112-120) (Year: 2014).*
Xiang et al. (Acta Biochim Biophys Sin 2014, 46: 1007-1010) (Year: 2014).*
MiRBase. "What do the miRNA names/identifiers mean?" obtained from https://www.mirbase.org/help/nomenclature.shtml on May 19, 2022, 2 pages (Year: 2022).*
Greiner, et al., "Principles and Practical Application of the Receiver-Operating Characteristics Analysis of Diagnostic Tests," *Preventative Veterinary Medicine*, 45; 23-41, 2000.

(Continued)

*Primary Examiner* — Juliet C Switzer

(57) ABSTRACT

The current disclosure relates to therapeutic treatments and diagnostic methods for esophageal cancer based on the expression level of biomarker miRNAs. Aspects of the disclosure relate to a method of treating esophageal cancer (EC) in a patient, said method comprising: diagnosing the patient with esophageal cancer when the patient is determined to have an elevated or decreased level of expression of one or more miRNAs selected from mir-15b, miR-17, mir-18a, mir-21, mir-23a, mir-24-2, mir-25, mir-27a, mir-93, mir-103, mir-106b, mir-129-2, mir-139, mir-146b, mir-148a, mir-151, miR-155, mir-181a-1, mir-181a, mir-181b-1, mir-181b, mir-182, mir-183, mir-192, mir-194-1, mir-194-2, mir-196a-1, mir-196a-2, mir-196b, mir-205, mir-215, mir-223, mir-224, mir-335, mir-338, mir-375, mir-421, mir-484, mir-505, mir-769, mir-944, mir-1468, mir-3648, and let-7i in a sample from a patient relative to the expression level of the one or more miRNAs in a control sample; and administering an effective amount of an esophageal treatment to the diagnosed patient.

9 Claims, 25 Drawing Sheets

(56) References Cited

OTHER PUBLICATIONS

International Preliminary Report on Patentability Issued in Corresponding PCT Application No. PCT/IB2017/054800, dated Feb. 5, 2019.
International Search Report and Written Report Issued in Corresponding PCT Application No. PCT/IB2017/054800, dated Feb. 2, 2018.
Youden, "Index of Rating Diagnostic Tests," *Cancer*, 3; 32-35, 1950.
Zweig & Campbell, "Receiver-Operating Characteristic (ROC) Plots: A Fundamental Evaluation Tool in Clinical Medicine," *Clinical Chemistry*, 39(4); 561-577, 1993.
Affymetrix: GeneChip miRNA 3.0 Array, Available at: <http://www.carrerasresearch.org/en/genechip-mirna-3-0-array_38713.pdf> [Accessed Mar. 29, 2012].
Guan, et al., "MiR-613: A Novel Diagnostic and Prognostic Biomarker for Patients with Esophageal Squamous Cell Carcinoma," *Tumor Biology*, 37(4): 4383-4391, 2015.
Guo, et al., "Distinctive MicroRNA Profiles Relating to Patient Survival in Esophageal Squamous Cell Carcinoma," *Cancer Research*, 68(1): 26-33, 2008.
Harada, et al., "The Role of MicroRNA in Esophageal Squamous Cell Carcinoma," *Journal of Gastroenterology*, 51(6): 520-530, 2016.
Komatsu, et al., "Circulating microRNAs in Plasma of Patients with Oesophageal Squamous Cell Carcinoma," *British Journal of Cancer*, 105(1): 104-111, 2011.
Komatsu, et al., "Plasma MicroRNA Profiles: Identification of miR-25 as a Novel Diagnostic and Monitoring Biomarker in Oesophageal Squamous Cell Carcinoma," *British Journal of Cancer*, 111(8): 1614-1624, 2014.
Search Report Issued in Corresponding European Patent Application No. EP 17836511.0, dated Feb. 24, 2020.
Zhang, et al., "Expression Profile of MicroRNAs in Serum: A Fingerprint for Esophageal Squamous Cell Carcinoma," *Clinical Chemistry*, 56(12): 1871-1879, 2010.

* cited by examiner

| Rank | miRNA Combinations | AUC | Sens | Spec |
|---|---|---|---|---|
| 1 | miR-21, 93, 27a, 24-2, 17 | 1.00 | 100 | 100 |
| 1 | miR-21, 93, 27a, 24-2 | 1.00 | 100 | 100 |
| 1 | miR-93, 27a, 24-2, 17 | 1.00 | 100 | 100 |
| 1 | miR-21, 93, 27a, 17 | 1.00 | 100 | 100 |
| 1 | miR-21, 93, 17 | 1.00 | 100 | 100 |
| 6 | miR-93, 27a, 17 | 0.996 | 100 | 96.4 |
| 7 | miR-93, 24-2 | 0.995 | 100 | 92.8 |
| 8 | miR-93, 27a | 0.994 | 100 | 92.8 |
| 9 | miR-93, 17 | 0.994 | 100 | 92.8 |
| 10 | miR-93, 21 | 0.989 | 88.8 | 100 |

FIG. 5A

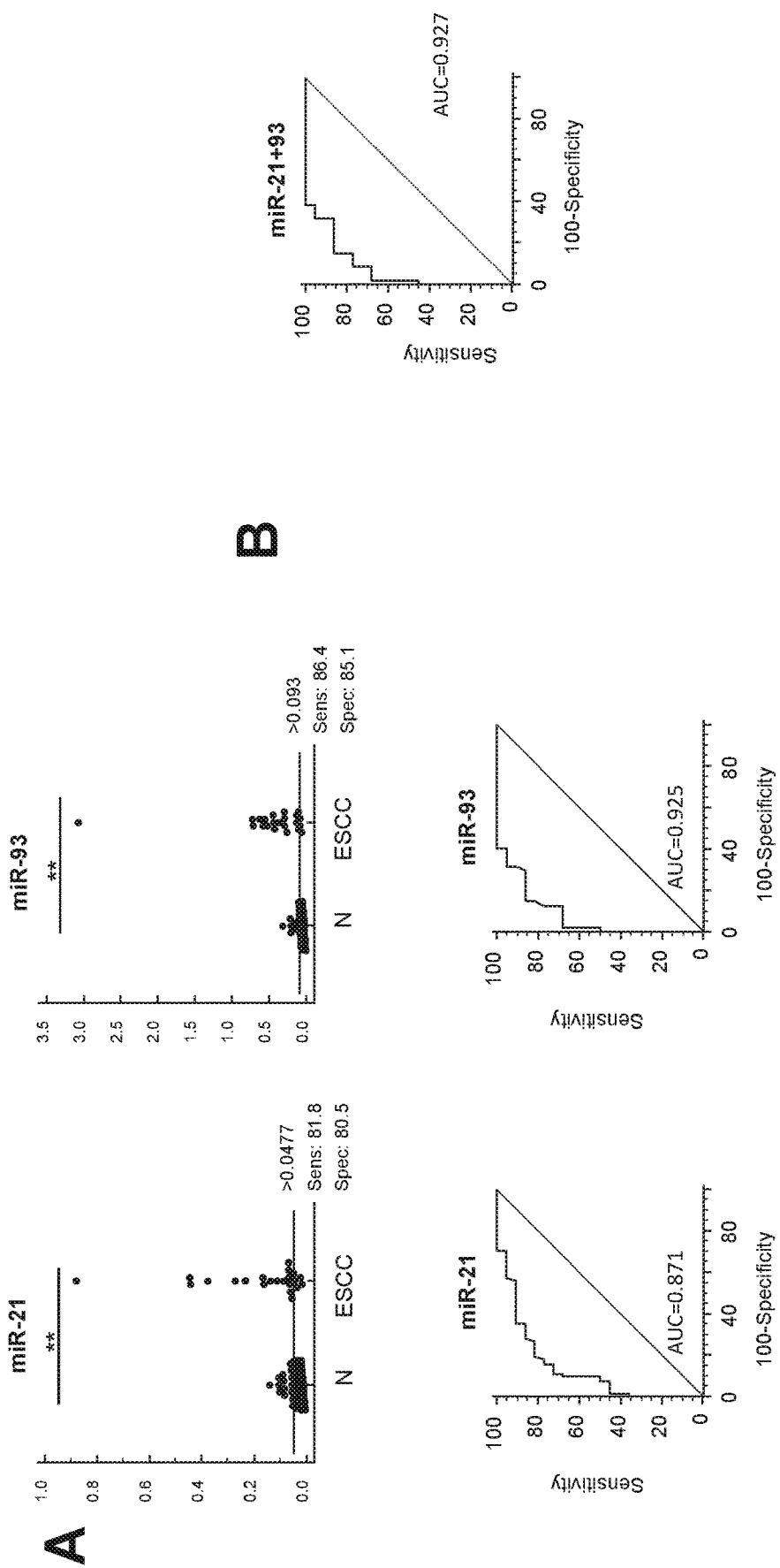
FIG. 6A-B

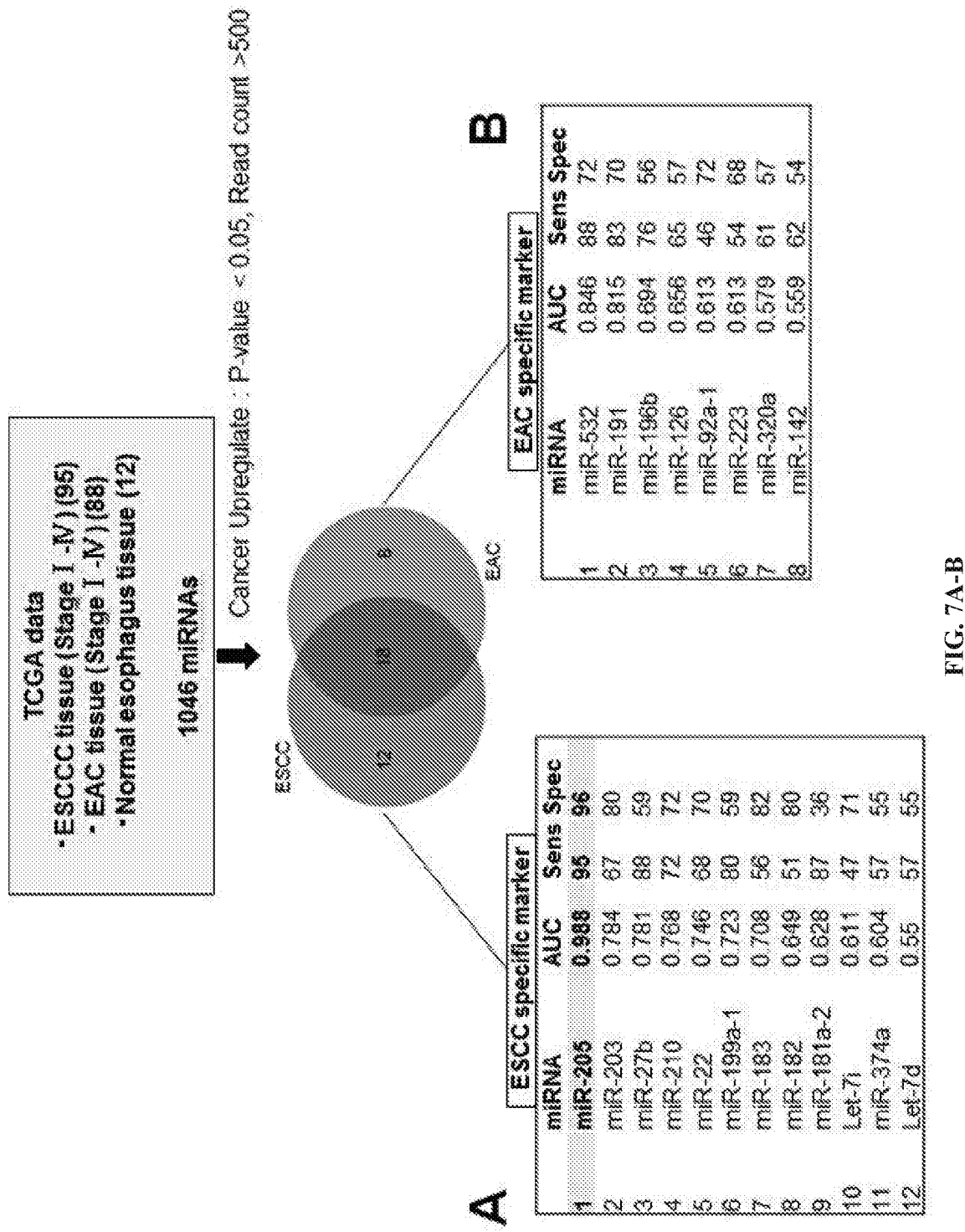
FIG. 7A-B

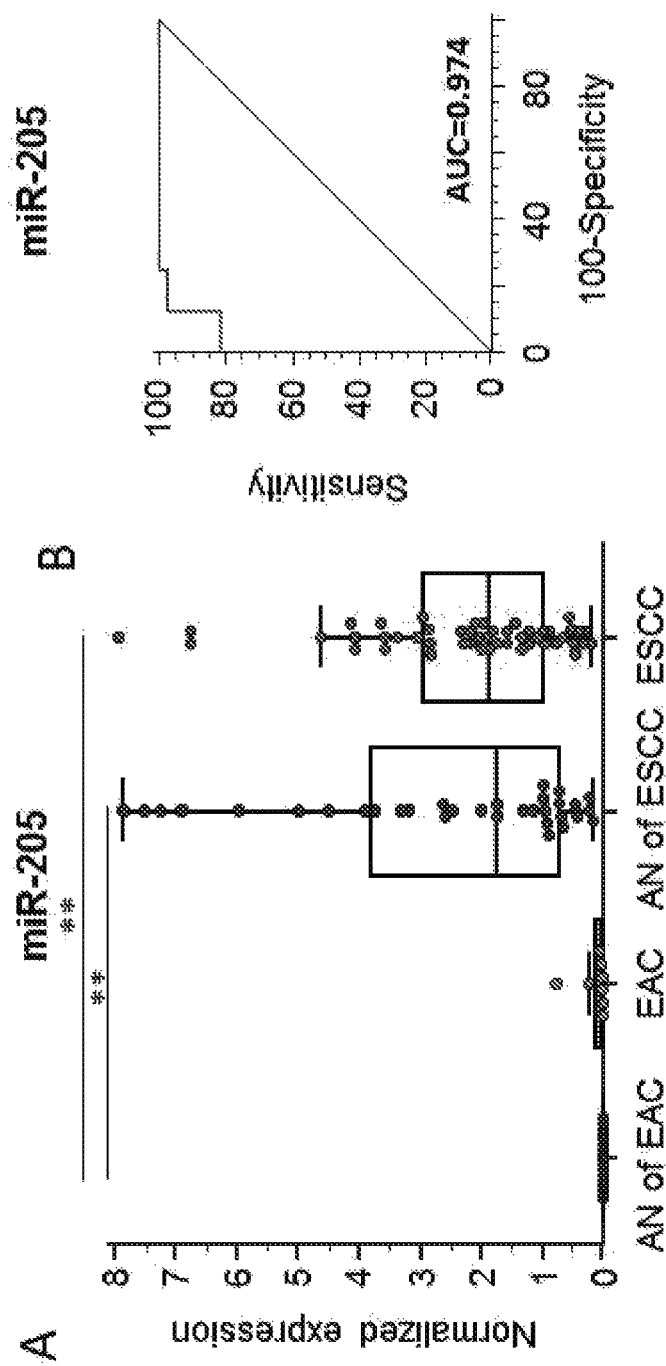
FIG. 8A-B

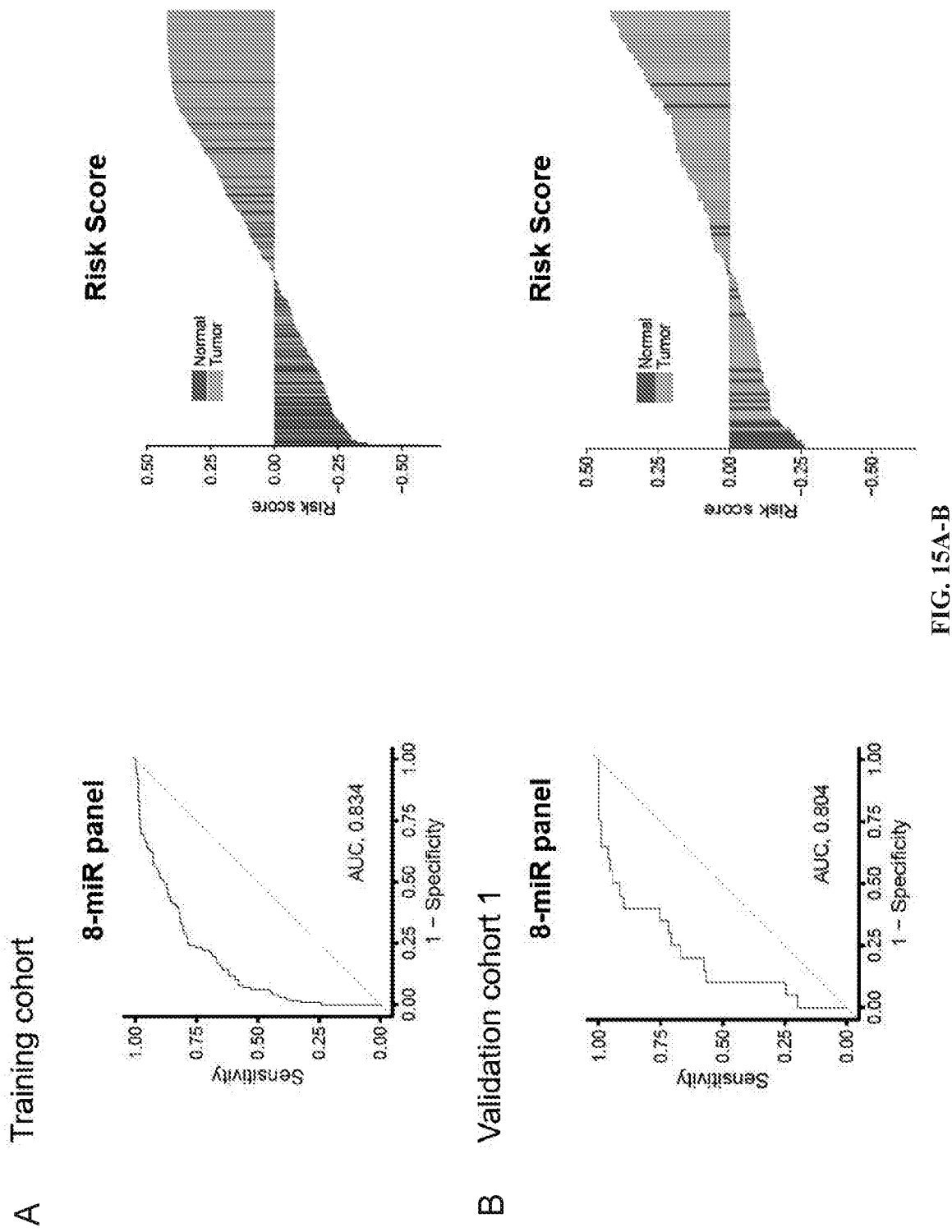
FIG. 15A-B

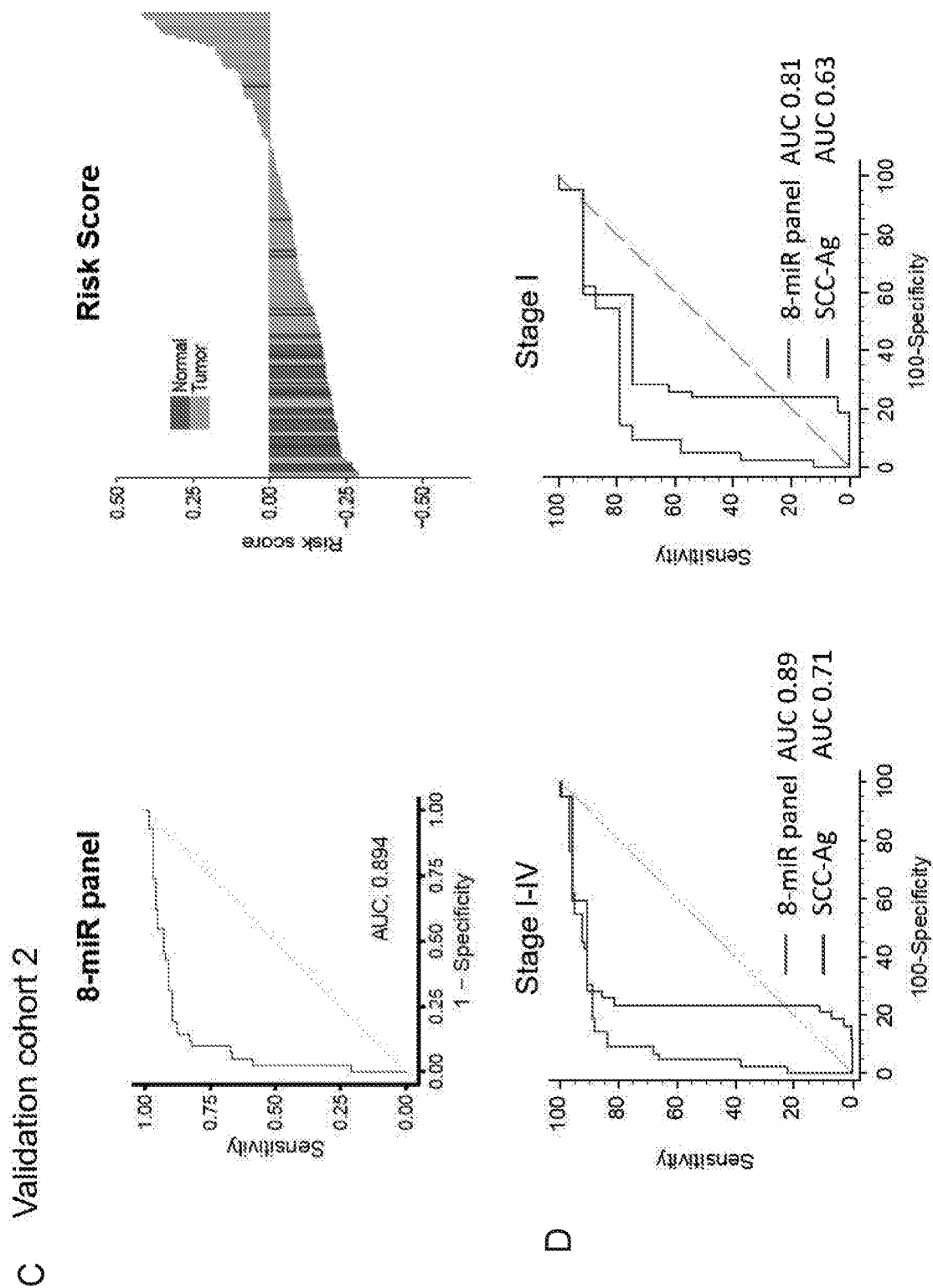
FIG. 15C-D

METHODS FOR DIAGNOSING AND TREATING ESOPHAGEAL CANCER

This application is a national phase under 35 U.S.C. § 371 of International Application No. PCT/IB2017/054800, filed Aug. 4, 2017, which claims the benefit of priority to U.S. Provisional Patent Application Ser. No. 62/371,028, filed Aug. 4, 2016, the entire contents of each of which are hereby incorporated by reference in their entirety.

STATEMENT OF GOVERNMENT SUPPORT

This invention was made with government support under Grant No. R01 CA184792 awarded by the National Institutes of Health. The government has certain rights in the invention.

BACKGROUND OF THE INVENTION

1. Field of the Invention

The present invention relates generally to the fields of molecular biology and oncology. More particularly, it concerns methods and compositions involving microRNA (miRNAs) molecules and cancer prognosis, diagnosis, and treatment.

2. Description of Related Art

Esophageal cancer occurs when cancer cells develop in the esophagus, a tube-like structure that runs from your throat to your stomach. Food goes from the mouth to the stomach through the esophagus. The cancer starts at the inner layer of the esophagus and can spread throughout the other layers of the esophagus and to other parts of the body (metastasis).

There are two main types of esophageal cancer. One type is esophagus squamous-cell carcinoma. Squamous cells line the inner esophagus, and cancer developing from squamous cells can occur along the entire esophagus. The other type is called esophagus adenocarcinoma. This is cancer that develops from gland cells. To develop adenocarcinoma of the esophagus, squamous cells that normally line the esophagus are replaced by gland cells. This typically occurs in the lower esophagus near the stomach and is believed to be largely related to acid exposure to the lower esophagus.

Esophageal cancer (EC) is the sixth leading cause of cancer-related death and the eighth most common cancer worldwide, with occurrence rates varying greatly by geographic locations and ethnicity. Esophageal squamous cell carcinoma (ESCC) accounts for almost 80% of all EC cases, and is particularly high in Eastern Asia and Eastern and Southern Africa. The average 5-year survival rate for all ESCC is approximately 10-41%. One of the main reasons for its poor prognosis is that esophagus has no serosa and has an extensive network of lymphatics, reducing the resistance against local spread of cancer and allowing for early regional tumor advancement and early metastasis. Furthermore, the early stages of ESCC typically have no symptoms, and consequently results in delayed diagnosis. Although various biochemical blood-based markers have been investigated in the diagnosis of ESCC patients, including carcinoembryonic antigen (CEA), squamous cell carcinoma antigen (SCC-Ag), cytokeratin-19 fragment (CYFRA21-1) and p53 antibody, these circulating biomarkers are not reliable for early detection of ESCC. Therefore, the discovery of novel circulating biomarkers for the early detection of ESCC is of utmost clinical importance for improving the overall outcome of ESCC patients.

Thus, there is a need in the art for more effective methods for the detection of, particularly the early detection of esophageal cancer. Furthermore, more accurate diagnosis of the CRC stage will lead to novel and more effective therapeutic methods for treating CRC.

SUMMARY OF THE INVENTION

The current disclosure fulfills a need in the art by providing more effective therapeutic treatments and diagnostic methods for esophageal cancer based on the expression level of biomarker miRNAs. Aspects of the disclosure relate to a method of treating esophageal cancer (EC) in a patient, said method comprising: diagnosing the patient with esophageal cancer when the patient is determined to have an elevated or decreased level of expression of one or more miRNAs selected from mir-15b, miR-17, mir-18a, mir-21, mir-23a, mir-24-2, mir-25, mir-27a, mir-93, mir-103, mir-106b, mir-129-2, mir-139, mir-146b, mir-148a, mir-151, miR-155, mir-181a-1, mir-181a, mir-181b-1, mir-181b, mir-182, mir-183, mir-192, mir-194-1, mir-194-2, mir-196a-1, mir-196a-2, mir-196b, mir-205, mir-215, mir-223, mir-224, mir-335, mir-338, mir-375, mir-421, mir-484, mir-505, mir-769, mir-944, mir-1468, mir-3648, and let-7i in a sample from a patient relative to the expression level of the one or more miRNAs in a control sample; and administering an effective amount of an esophageal treatment to the diagnosed patient.

Further aspects relate to a method for treating a patient determined to have esophageal cancer comprising: administering an esophageal cancer treatment to the patient, wherein the patient was determined to have an elevated or decreased level of expression of one or more miRNAs selected from mir-15b, miR-17, mir-18a, mir-21, mir-23a, mir-24-2, mir-25, mir-27a, mir-93, mir-103, mir-106b, mir-129-2, mir-139, mir-146b, mir-148a, mir-151, miR-155, mir-181a-1, mir-181a, mir-181b-1, mir-181b, mir-182, mir-183, mir-192, mir-194-1, mir-194-2, mir-196a-1, mir-196a-2, mir-196b, mir-205, mir-215, mir-223, mir-224, mir-335, mir-338, mir-375, mir-421, mir-484, mir-505, mir-769, mir-944, mir-1468, mir-3648, and let-7i in a sample from a patient relative to the expression level of the one or more miRNAs in a control sample.

Further aspects relate to a method of detecting one or more miRNAs in a patient, said method comprising: obtaining a sample from a human patient; and detecting whether the one or more miRNAs have elevated or reduced expression in the sample by contacting the sample with a miRNA detecting agent; wherein the one or more miRNAs are selected from from mir-15b, miR-17, mir-18a, mir-21, mir-23a, mir-24-2, mir-25, mir-27a, mir-93, mir-103, mir-106b, mir-129-2, mir-139, mir-146b, mir-148a, mir-151, miR-155, mir-181a-1, mir-181a, mir-181b-1, mir-181b, mir-182, mir-183, mir-192, mir-194-1, mir-194-2, mir-196a-1, mir-196a-2, mir-196b, mir-205, mir-215, mir-223, mir-224, mir-335, mir-338, mir-375, mir-421, mir-484, mir-505, mir-769, mir-944, mir-1468, mir-3648, and let-7i. In some embodiments, the method further comprises treating the patient for esophageal cancer when the one or more miRNAs are elevated in the sample from the patient. In some embodiments, the method further comprises comparing the expression level of the miRNA in the sample from the patient to the expression level of the miRNA in a control sample. In some embodiments, the sample comprises a serum sample. In some embodiments, the control sample comprises a biological sample from a human patient without esophageal cancer (EC). In some embodiments, the human patient is suspected as having esophageal cancer.

Further aspects of the disclosure relate to a method for treating a patient determined to have esophageal cancer comprising: administering an esophageal cancer treatment to the patient, wherein the patient was determined to have an elevated level of expression of one or more miRNAs selected from miR-103, miR-106b, miR-151, miR-17, miR-181a, miR-21, miR-25, and miR-93 in a sample from a patient relative to the expression level of the one or more miRNAs in a control sample. In some embodiments, the sample from the patient comprises a serum sample. In some embodiments, the esophageal cancer is esophagus squamous-cell carcinoma (ESCC).

Yet further aspects relate to a method for diagnosing a patient with esophageal cancer comprising: determining the level of expression of one or more miRNAs selected from mir-15b, miR-17, mir-18a, mir-21, mir-23a, mir-24-2, mir-25, mir-27a, mir-93, mir-103, mir-106b, mir-129-2, mir-139, mir-146b, mir-148a, mir-151, miR-155, mir-181a-1, mir-181a, mir-181b-1, mir-181b, mir-182, mir-183, mir-192, mir-194-1, mir-194-2, mir-196a-1, mir-196a-2, mir-196b, mir-205, mir-215, mir-223, mir-224, mir-335, mir-338, mir-375, mir-421, mir-484, mir-505, mir-769, mir-944, mir-1468, mir-3648, and let-7i in a sample from a patient; and diagnosing esophageal cancer based on the expression level of the one or more miRNAs.

It is contemplated that any methods or kits described herein may involve, may involve at least, or may involve at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, or 44 (or any range derivable therein) of the following miRNAs: mir-15b, miR-17, mir-18a, mir-21, mir-23a, mir-24-2, mir-25, mir-27a, mir-93, mir-103, mir-106b, mir-129-2, mir-139, mir-146b, mir-148a, mir-151, miR-155, mir-181a-1, mir-181a, mir-181b-1, mir-181b, mir-182, mir-183, mir-192, mir-194-1, mir-194-2, mir-196a-1, mir-196a-2, mir-196b, mir-205, mir-215, mir-223, mir-224, mir-335, mir-338, mir-375, mir-421, mir-484, mir-505, mir-769, mir-944, mir-1468, mir-3648, and let-7i. In some embodiments, expression of one or more of these miRNA molecules may be detected, measured, compared to, recorded, analyzed, characterized, and/or qualified. In some embodiments, the patient is diagnosed with EC when the expression level of the one or more detected miRNAs is significantly different compared to a control sample.

In some embodiments, the method further comprises obtaining a sample from the patient. In some embodiments, the level of expression of the one or more miRNAs is elevated in comparison to a control. In some embodiments, the level of expression of the one or more miRNAs is decreased in comparison to a control.

Embodiments concern determining that the level of expression of a miRNA. In some embodiments, that level is compared to a control in order to determine whether the expression level or activity of the miRNA is elevated as compared to the level in non-cancerous biological sample. The control may be a non-cancerous esophageal tissue or it may be a cancerous esophageal tissue. If the control is a cancerous tissue, a sample may be determined to have an elevated level of miRNA because the levels in the control and the patient sample are similar, such as within, at least or at most 1, 2, 3, or 4 standard deviations (or any range derivable therein) of one another. In some embodiments, the control is the level of the one or more miRNAs in a non-EC patient sample. In some embodiments, the control sample is a non-cancerous biological sample. In some embodiments, the control is from a particular cohort described herein. It is contemplated that one or more controls may be measured at the same time as a test sample or it may be a normalized value collected from multiple control samples.

In some embodiments, the method further comprises determining the level of expression of the one or more miRNAs in the sample from the patient.

In some embodiments, the one or more miRNAs comprise one or more of mir-21, mir-93, mir-106b, mir-27a, mir-17 and/or mir-181a. In some embodiments, the one or more miRNAs comprise mir-93. In some embodiments, the one or more miRNAs comprise mir-93 and mir-21. In some embodiments, the one or more miRNAs comprise mir-181a, mir-21, and mir-17. In some embodiments, the one or more miRNAs comprise mir-181a, mir-17, mir-21, and mir-27a. In some embodiments, the one or more miRNAs comprise mir-21, mir-93, and mir-27a.

In some embodiments, the one or more miRNAs comprise an elevated level of mir-205.

In some embodiments, the one or more miRNAs comprise an elevated level of one or more of miR-21, miR-93, miR-27a, miR-24-2, and miR-17, compared to a control. In some embodiments, the patient is treated for EC or diagnosed with EC, when the expression level of one or more of miR-21, miR-93, miR-27a, miR-24-2, and miR-17 is elevated compared to a control, such as the level of expression of the miRNA in a non-EC or non-cancerous control.

In some embodiments, the one or more miRNAs comprise an elevated level of one or more of miR-103, miR-106b, miR-151, miR-17, miR-181a, miR-21, miR-25, and miR-93, compared to a control. In some embodiments, the patient is treated for EC or diagnosed with EC, when the expression level of one or more of miR-103, miR-106b, miR-151, miR-17, miR-181a, miR-21, miR-25, and miR-93 is elevated compared to a control, such as the level of expression of the miRNA in a non-EC or non-cancerous control.

In some embodiments, the one or more miRNAs comprise at least two of mir-103, mir-106b, mir-151, mir-17, miR-181a, mir-21, miR-25, and mir-93. In some embodiments, the one or more miRNAs comprise at least two, three, four, five, six, seven, or eight of mir-103, mir-106b, mir-151, mir-17, miR-181a, mir-21, miR-25, and mir-93. In some embodiments, the one or more miRNAs comprise at least two of mir-103, mir-106b, mir-17, miR-181a, mir-21, miR-25, and mir-93.

In some embodiments, the one or more miRNAs comprise let-7i, mir-103, mir-106b, mir-17, mir-151, mir-155, mir-181a, mir-181b, mir-182, mir-183, mir-18a, mir-21, mir-223, mir-23a, mir-25, mir-484, mir-505, and mir-93.

In some embodiments, the esophageal cancer is esophagus squamous-cell carcinoma (ESCC).

In some embodiments, the one or more miRNAs comprise an elevated level of mir-196a-1, mir-196b, and/or mir-21. In some embodiments, the esophageal cancer is esophagus adenocarcinoma (EAC).

In some embodiments, the patient sample and/or control sample is a tissue sample. In some embodiments, the patient sample and/or control sample is a serum sample. In some embodiments, the patient sample and/or control sample is a biological sample as described herein.

In some embodiments, the esophageal cancer treatment comprises chemotherapy, radiation therapy, surgery, or combinations thereof. In some embodiments, the chemotherapy comprises carboplatin, paclitaxel, cisplatin, 5-fluorouracil, epirubicin, docetaxel, cepecitabine, oxaliplatin, and combinations thereof.

In some embodiments, the method further comprises measuring the expression level of the one or more miRNAs in a biological sample from the patient. In some embodiments, the method further comprises comparing the expression level of the one or more miRNAs in a biological sample from the patient to the expression level of the one or more miRNAs in a control biological sample.

In some embodiments, the patient has or is determined to have Stage I, IA, IB, II, IIA, IIB, III, IIIA, IIIB, IIIC, or IV esophageal cancer. In some embodiments, the patient has or is determined to have, or the method is for diagnosis of early stage EC or stage I EC, such as ESCC. In some embodiments, the biological sample from the patient is a sample from a primary tumor. In some embodiments, the esophageal cancer comprises category T1, T2, T3, or T4 esophageal cancer. In some embodiments, the esophageal cancer comprises category N0, N1, N2, or N3 esophageal cancer. In some embodiments, the esophageal cancer comprises category M0 or M1 esophageal cancer. In some embodiments, the esophageal cancer comprises lymph node metastasis. In some embodiments, the esophageal cancer comprises distant metastasis. In some embodiments, the distant metastases are lung, liver, and/or bone metastasis. In some embodiments, the esophageal cancer comprises one or more aspects of EC described herein. In some embodiments, the method is for distinguishing between one or more stages or types of EC described herein.

In some embodiments, the elevated or decreased level of expression is determined from a cut-off value. In some embodiments, the cut-off value is determined by a ROC analysis.

In some embodiments, the patient has previously been treated for esophageal cancer.

In some embodiments, the miRNA marker is for distinguishing between EAC and ESCC or between EAC and no EC or between ESCC and no EC. In some embodiments, the EAC-specific marker, which may discriminate between EAC and ESCC or EAC and no EC comprises one or more of mir-196a-1, mir-196b, mir-21, mir-181a-1, mir-196a-2, mir-335, mir-181b-1, mir-15b, mir-17, and mir-106b. In some embodiments, the ESCC-specific marker, which may discriminate between ESCC and EAC or ESCC and no EC comprises one or more of mir-205, mir-944, mir-194-2, mir-192, mir-194-1, mir-23a, mir-215, mir-27a, mir-338, and/or mir-21.

Further aspects of the disclosure relate to a kit comprising an agent for detecting one or more miRNAs selected from mir-15b, miR-17, mir-18a, mir-21, mir-23a, mir-24-2, mir-25, mir-27a, mir-93, mir-103, mir-106b, mir-129-2, mir-139, mir-146b, mir-148a, mir-151, miR-155, mir-181a-1, mir-181a, mir-181b-1, mir-181b, mir-182, mir-183, mir-192, mir-194-1, mir-194-2, mir-196a-1, mir-196a-2, mir-196b, mir-205, mir-215, mir-223, mir-224, mir-335, mir-338, mir-375, mir-421, mir-484, mir-505, mir-769, mir-944, mir-1468, mir-3648, and let-7i. In some embodiments, the agent comprises one or more nucleic acid probes for amplification of the miRNAs from a biological sample. In some embodiments, the agent is labeled. In some embodiments, the kit further comprises instructions for use.

In some aspects, the disclosure relates to a kit comprising agents for detecting EC-differentially expressed miRNAs, wherein the differentially expressed miRNAs consist of mir-21, mir-93, mir-106b, mir-27a, mir-17 and mir-181a. In some aspects, the disclosure relates to a kit comprising agents for detecting an EC-differentially expressed miRNA, wherein the differentially expressed miRNA consists of mir-205. In some embodiments, the disclosure relates to a kit comprising agents for detecting an EC-differentially expressed miRNA, wherein the differentially expressed miRNA consists of mir-196a-1. In some embodiments, the disclosure relates to a kit comprising agents for detecting an EC-differentially expressed miRNA, wherein the differentially expressed miRNA consists of mir-196b. In some embodiments, the disclosure relates to a kit comprising agents for detecting an EC-differentially expressed miRNA, wherein the differentially expressed miRNA consists of mir-21. In some embodiments, the disclosure relates to a kit comprising agents for detecting an EC-differentially expressed miRNA, wherein the differentially expressed miRNA consists of mir-103, mir-106b, mir-151, mir-17, mir-181a, mir-21, mir-25, and mir-93. In some embodiments, the disclosure relates to a comprising agents for detecting EC-differentially expressed miRNAs, wherein the differentially expressed miRNAs consist of let-7i, mir-103, mir-106b, mir-17, mir-151, mir-155, mir-181a, mir-181b, mir-182, mir-183, mir-18a, mir-21, mir-223, mir-23a, mir-25, mir-484, mir-505, and mir-93.

In some embodiments, the kit further comprises one or more agents for detecting one or more controls. In some embodiments, the kit further comprises reagents for isolating nucleic acids from a biological sample. In some embodiments, the reagents are for isolating nucleic acids from a serum sample. In some embodiments, the reagents are for isolating nucleic acids from a sample described herein.

The term subject or patient may refer to an animal (for example a mammal), including but not limited to humans, non-human primates, rodents, dogs, or pigs. The methods of obtaining provided herein include methods of biopsy such as fine needle aspiration, core needle biopsy, vacuum assisted biopsy, incisional biopsy, excisional biopsy, punch biopsy, shave biopsy or skin biopsy.

In certain embodiments the sample is obtained from a biopsy from esophageal, stomach or the muscle tissue, mucosa or submucosa thereof. In other embodiments the sample may be obtained from any of the tissues provided herein that include but are not limited to gall bladder, skin, heart, lung, breast, pancreas, liver, muscle, kidney, smooth muscle, bladder, intestine, brain, prostate, or thyroid tissue.

Alternatively, the sample may include but not be limited to blood, serum, sweat, hair follicle, buccal tissue, tears, menses, urine, feces, or saliva. In particular embodiments, the sample may be a tissue sample, a whole blood sample, a urine sample, a saliva sample, a serum sample, a plasma sample or a fecal sample.

In certain aspects the sample is obtained from cystic fluid or fluid derived from a tumor or neoplasm. In yet other embodiments the cyst, tumor or neoplasm is in the digestive system. In certain aspects of the current methods, any medical professional such as a doctor, nurse or medical technician may obtain a biological sample for testing. In further aspects of the current methods, the patient or subject may obtain a biological sample for testing without the assistance of a medical professional, such as obtaining a whole blood sample, a urine sample, a fecal sample, a buccal sample, or a saliva sample.

In further embodiments, the sample may be a fresh, frozen or preserved sample or a fine needle aspirate. In particular embodiments, the sample is a formalin-fixed, paraffin-embedded (FFPE) sample. An acquired sample may be placed in short term or long term storage by placing in a suitable medium, excipient, solution, or container. In certain cases storage may require keeping the sample in a refrigerated, or frozen environment. The sample may be quickly frozen prior to storage in a frozen environment. In certain instances the frozen sample may be contacted with a suitable cryopreservation medium or compound. Examples of cryopreservation mediums or compounds include but are not limited to: glycerol, ethylene glycol, sucrose, or glucose.

Some embodiments further involve isolating nucleic acids such as ribonucleic or RNA from a biological sample or in a sample of the patient. Other steps may or may not include amplifying a nucleic acid in a sample and/or hybridizing one or more probes to an amplified or non-amplified nucleic acid. The methods may further comprise assaying nucleic acids in a sample. In certain embodiments, a microarray may be used to measure or assay the level of miRNA expression in a sample. The methods may further comprise recording the miRNA expression level in a tangible medium or reporting the expression level to the patient, a health care payer, a physician, an insurance agent, or an electronic system.

A difference between or among weighted coefficients ore expression levels or between or among the weighted comparisons may be, be at least or be at most about 0.1, 0.2, 0.3, 0.4, 0.5, 0.6, 0.7, 0.8, 0.9, 1.1, 1.2, 1.3, 1.4, 1.5, 1.6, 1.7, 1.8, 1.9, 2.0, 2.5, 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 15.5, 16.0, 16.5, 17.0, 17.5, 18.0, 18.5, 19.0, 19.5, 20.0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 410, 420, 425, 430, 440, 441, 450, 460, 470, 475, 480, 490, 500, 510, 520, 525, 530, 540, 550, 560, 570, 575, 580, 590, 600, 610, 620, 625, 630, 640, 650, 660, 670, 675, 680, 690, 700, 710, 720, 725, 730, 740, 750, 760, 770, 775, 780, 790, 800, 810, 820, 825, 830, 840, 850, 860, 870, 875, 880, 890, 900, 910, 920, 925, 930, 940, 950, 960, 970, 975, 980, 990, 1000 times or —fold (or any range derivable therein).

In some embodiments, determination of calculation of a diagnostic, prognostic, or risk score is performed by applying classification algorithms based on the expression values of biomarkers with differential expression p values of about, between about, or at most about 0.005, 0.006, 0.007, 0.008, 0.009, 0.01, 0.011, 0.012, 0.013, 0.014, 0.015, 0.016, 0.017, 0.018, 0.019, 0.020, 0.021, 0.022, 0.023, 0.024, 0.025, 0.026, 0.027, 0.028, 0.029, 0.03, 0.031, 0.032, 0.033, 0.034, 0.035, 0.036, 0.037, 0.038, 0.039, 0.040, 0.041, 0.042, 0.043, 0.044, 0.045, 0.046, 0.047, 0.048, 0.049, 0.050, 0.051, 0.052, 0.053, 0.054, 0.055, 0.056, 0.057, 0.058, 0.059, 0.060, 0.061, 0.062, 0.063, 0.064, 0.065, 0.066, 0.067, 0.068, 0.069, 0.070, 0.071, 0.072, 0.073, 0.074, 0.075, 0.076, 0.077, 0.078, 0.079, 0.080, 0.081, 0.082, 0.083, 0.084, 0.085, 0.086, 0.087, 0.088, 0.089, 0.090, 0.091, 0.092, 0.093, 0.094, 0.095, 0.096, 0.097, 0.098, 0.099, 0.1, 0.2, 0.3, 0.4, 0.5, 0.6, 0.7, 0.8, 0.9 or higher (or any range derivable therein). In certain embodiments, the prognosis score is calculated using one or more statistically significantly differentially expressed biomarkers (either individually or as difference pairs).

Any of the methods described herein may be implemented on tangible computer-readable medium comprising computer-readable code that, when executed by a computer, causes the computer to perform one or more operations. In some embodiments, there is a tangible computer-readable medium comprising computer-readable code that, when executed by a computer, causes the computer to perform operations comprising: a) receiving information corresponding to an expression level of a gene encoding a miRNA in a sample from a patient; and b) determining a difference value in the expression levels using the information corresponding to the expression levels in the sample compared to a control or reference expression level for the gene.

In other aspects, tangible computer-readable medium further comprise computer-readable code that, when executed by a computer, causes the computer to perform one or more additional operations comprising making recommendations comprising: wherein the patient in the step a) is under or after a first treatment for esophageal cancer, administering the same treatment as the first treatment to the patient if the patient does not have increased expression level; administering a different treatment from the first treatment to the patient if the patient has increased expression level.

In some embodiments, receiving information comprises receiving from a tangible data storage device information corresponding to the expression levels from a tangible storage device. In additional embodiments the medium further comprises computer-readable code that, when executed by a computer, causes the computer to perform one or more additional operations comprising: sending information corresponding to the difference value to a tangible data storage device, calculating a prognosis score for the patient, treating the patient with a traditional esophageal therapy if the patient does not have expression levels, and/or or treating the patient with an alternative esophageal therapy if the patient has increased expression levels.

The tangible, computer-readable medium further comprise computer-readable code that, when executed by a computer, causes the computer to perform one or more additional operations comprising calculating a prognosis score for the patient. The operations may further comprise making recommendations comprising: administering a treatment to a patient that is determined to have a decreased expression level.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. The methods and kits described above as comprising the recited claim elements may also include embodiments in which the methods consist of or consist essentially of the recited claim elements.

The term consisting essentially of, as used herein with respect to compositions, is intended to mean that the active ingredients in the composition consist of only the active ingredients listed in the claims. Therefore, a composition consisting essentially of cisplatin and 5-fluorouracil, for example, would exclude any other active ingredients, but may include any other pharmaceutical excipients or carriers.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 5A-B: ESCC tissue cohort 1—miRNA combination by logistic regression model. Shown in A is the ranking of miRNA combinations in the order of AUC. Shown in B are ROC curve analysis of best combination miRNAs. 5 kinds of combination miRNAs demonstrated 100% sensitivity and 100% specificity.

FIG. 6A-B: Serum phase—ESCC serum. The data shown in A demonstrates that derum miR-21, 93 levels were significantly elevated in cancer. AUC values of serum miR-21, 93 were 0.871 and 0.925, respectively. Shown in B is the AUC value (0.927) of serum miR-21+93 combination by logistic regression model.

FIG. 7A-C: Discovery Phase—ESCC vs. EAC. Shown in A is the ranking of ESCC specific marker. miR205 is the marker with the highest sensitivity and specificity for distinguishing between ESCC and EAC. The AUC value of miR-205 is 0.998. Shown in B is the ranking of EAC specific marker. Shown in C is the miR-205 expression level and ROC curves analysis in ESCC vs. EAC.

FIG. 8A-B: Validation Phase—ESCC vs EAC by cohort 1 tissue miR-205. The data shown in A demonstrates that miR-205 level were significantly elevated in EACC. The data shown in B demonstrates that the AUC value of miR-205 to distinguish between ESCC and EAC is 0.974.

FIG. 9 shows the specificity and sensitivity of the indicated miRNA markers and combinations in the serum of the samples from the Asia cohort.

FIG. 10 shows the specificity and sensitivity of the indicated miRNA markers and combinations in the serum of the samples from the Western cohort.

FIG. 11 shows the specificity and sensitivity of the indicated miRNA markers and combinations in the serum of the samples from the African cohort.

FIG. 12 shows the specificity and sensitivity of the indicated miRNA markers and combinations in the serum when the data from the three cohorts is pooled.

FIG. 15A-Ds: Establishment, validation and diagnostic performance evaluation of 8-miRNA signature model. A) ROC curve and waterfall plot of distinguishing ESCC serum from healthy controls by 8-miRNA signature model in training cohort. B) ROC curve and waterfall plot of distinguishing ESCC serum from healthy controls by 8-miRNA signature model in validation cohort 1. C) ROC curve and waterfall plot of distinguishing ESCC serum from healthy controls by 8-miRNA signature model in validation cohort 2. D) Diagnostic performance evaluation of the 8-miRNA signature model. It could distinguish all stages of ESCC patients (stage I-IV, n=123) from healthy controls (n=42) and it was superior to SCC-Ag (AUC=0.89, 0.71, respectively) and it could distinguish stage I ESCC patients (n=20) from healthy controls (n=42) and it was superior to SCC-Ag (AUC=0.81, 0.63, respectively).

DESCRIPTION OF ILLUSTRATIVE EMBODIMENTS

Figure 1:
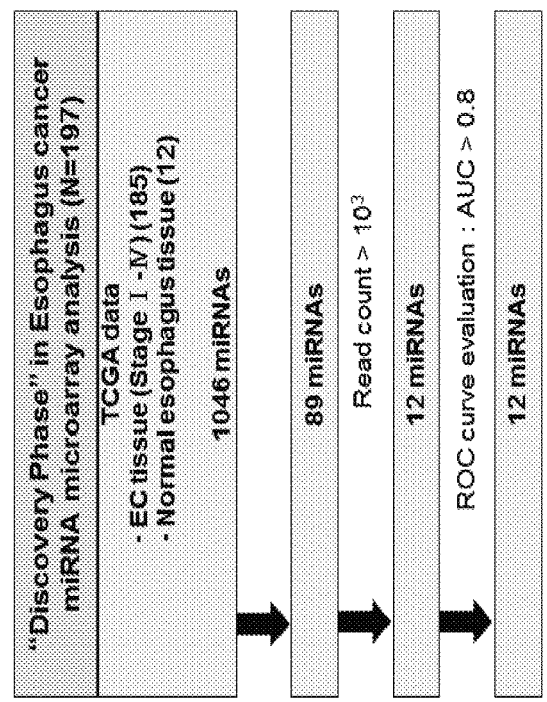
FIG. 1A-B: Esophagus cancer miRNA microarray analysis. Shown in A is a flowchart of the discovery phase of esophagus cancer. Twelve candidate miRNAs were selected. Shown in B is the ranking of candidate miRNAs in the order of AUC (area under the curve).
Figure 2:
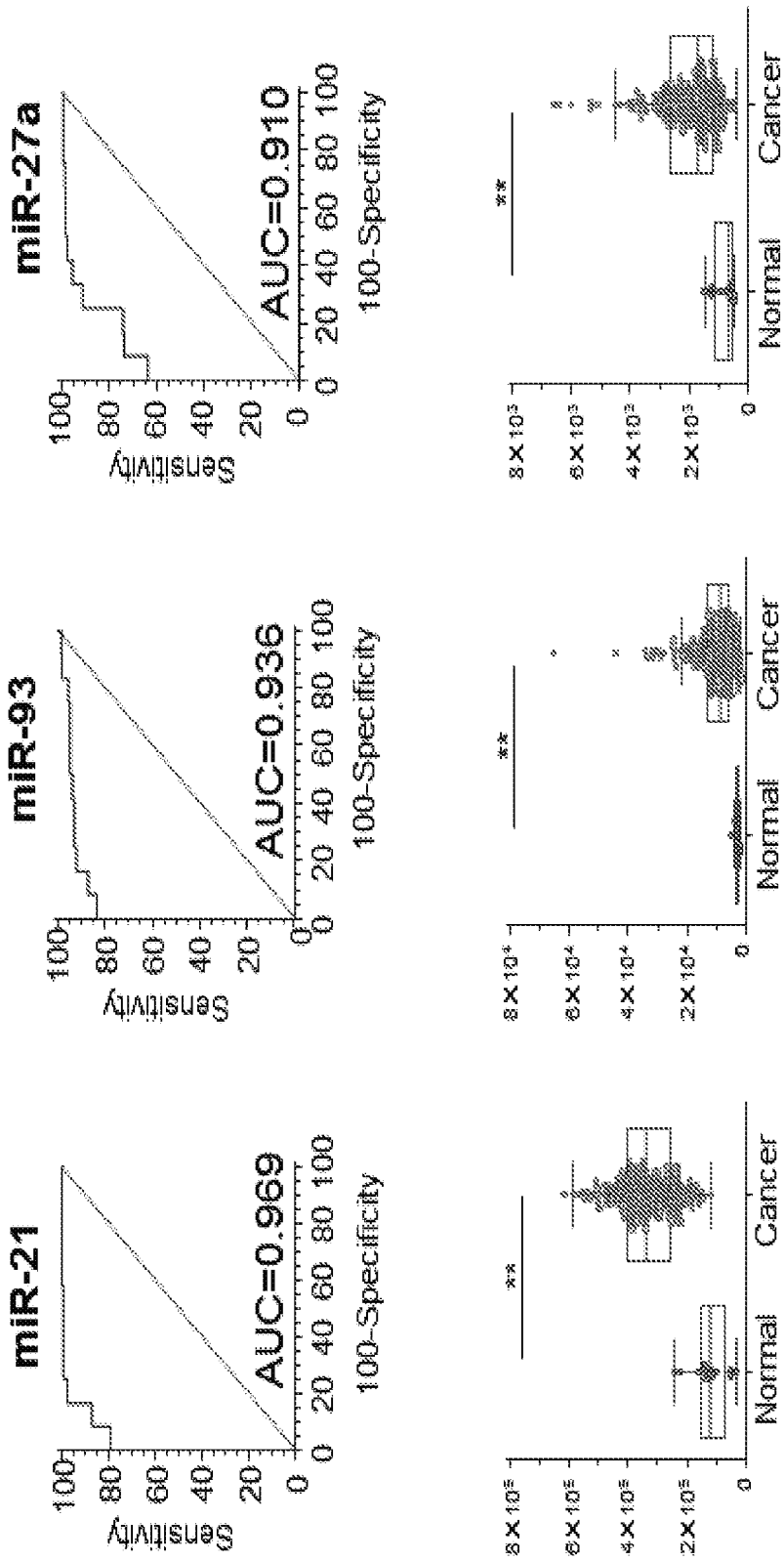
FIG. 2: Discovery Phase—Best miRNAs for Esophagus Cancer. Shown are ROC curve analysis and expression levels in normal vs. cancer of top five ranked miRNAs. miR-21, miR-93, miR-27a, miR-24-2, and miR-17 were significantly elevated in cancer.
Figure 2:
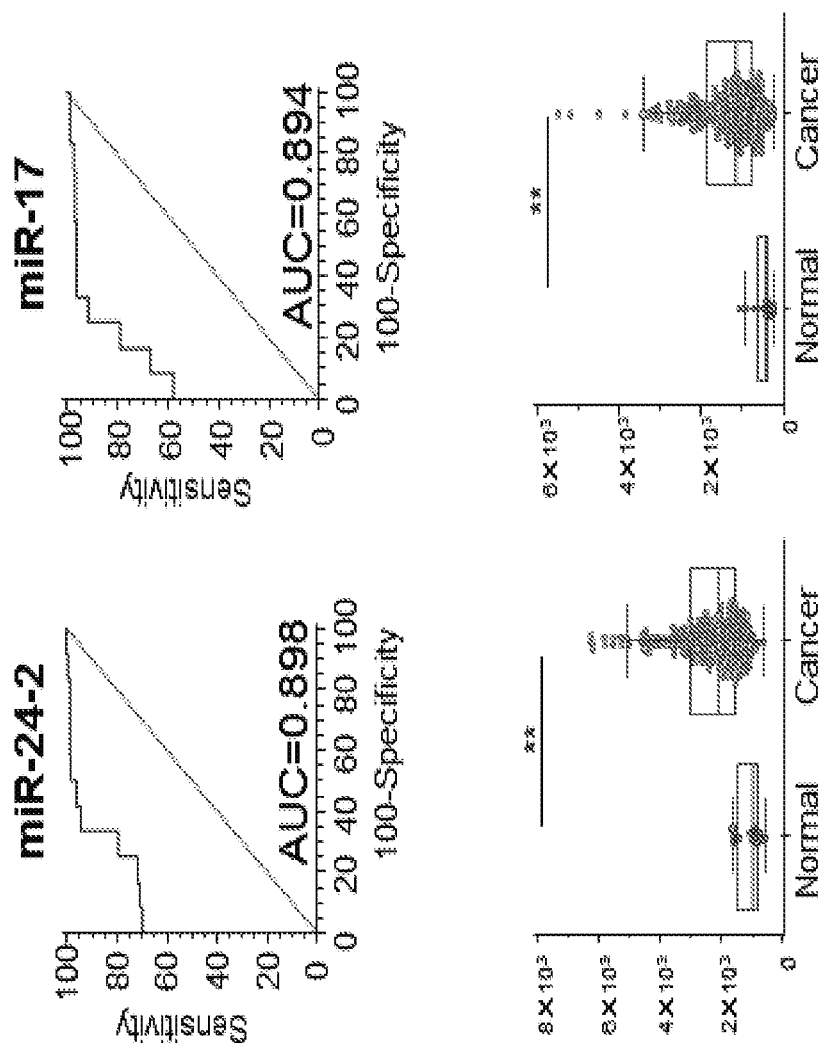
Figure 3:
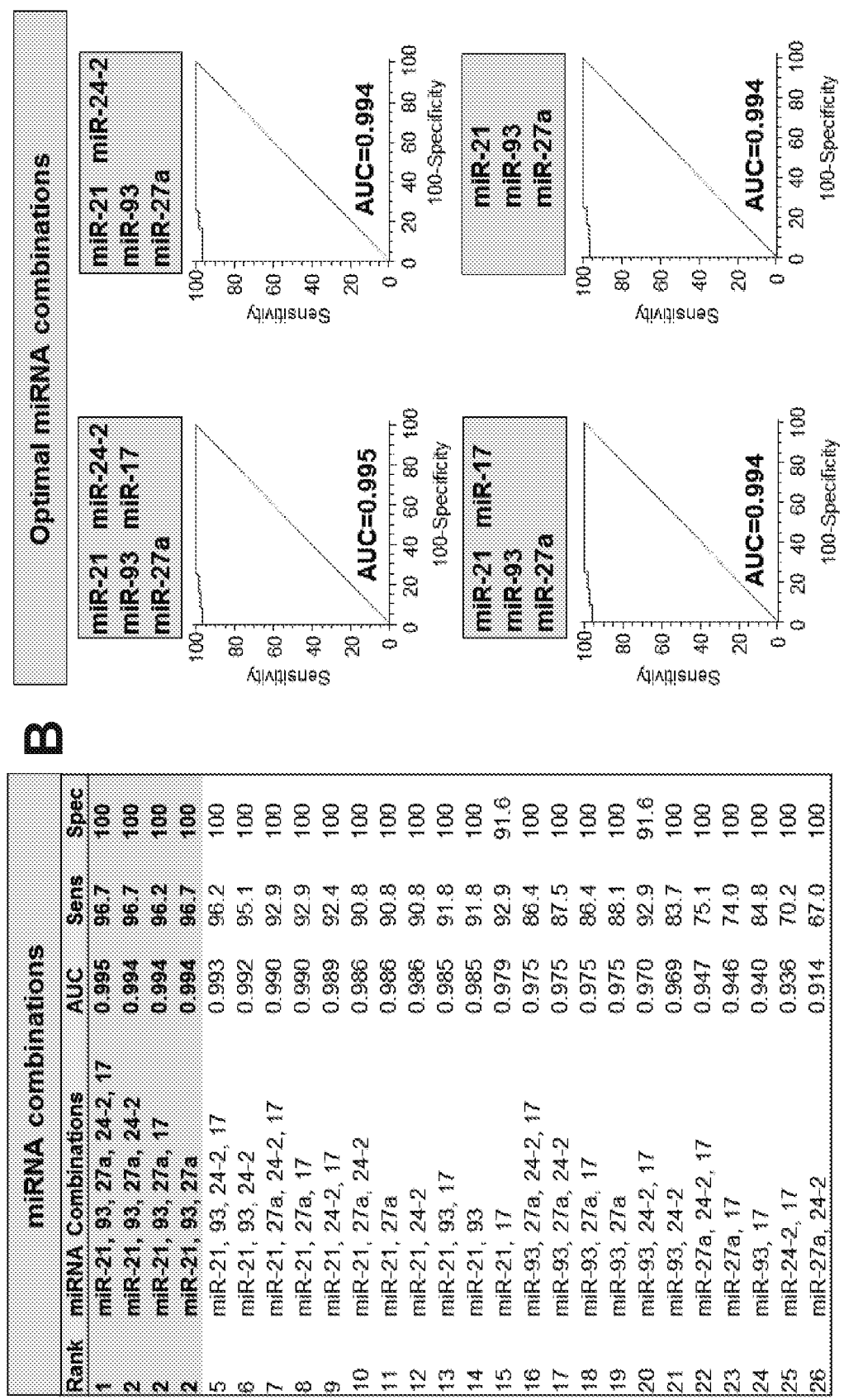
FIG. 3A-B: Esophagus cancer (EC) miRNA combination by logistic regression model. Shown in A is a ranking of miRNA combinations of top five ranked miRNAs in the order of AUC. Shown in B is ROC curve analysis about combinations of top four ranked miRNAs.
Figure 4:
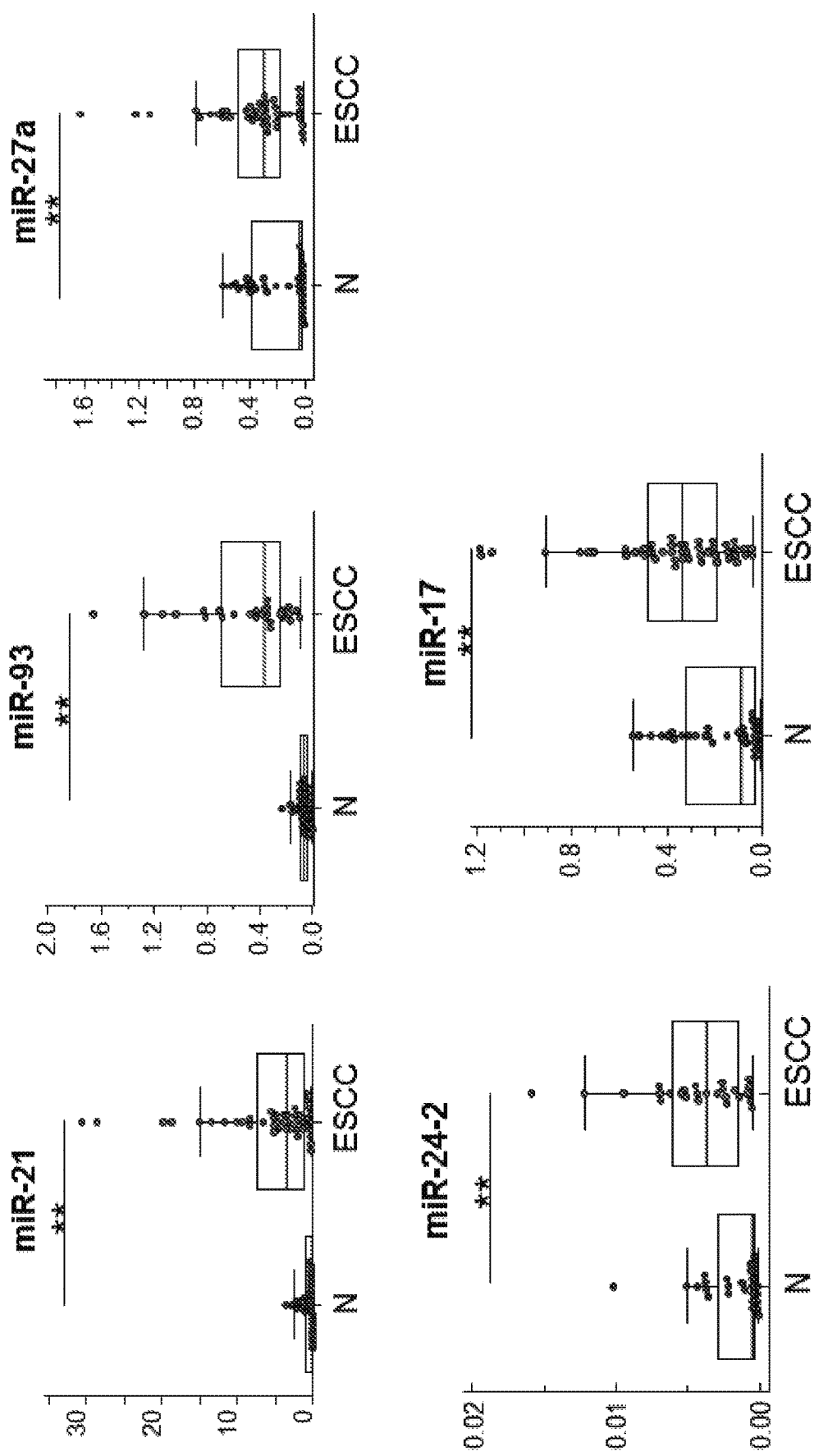
FIG. 4: ESCC tissue cohort 1. The levels of candidate top 5 miRNAs (mir-21, 93, 27a, 24-2, 17) were significantly elevated in cancer.
Figure 5B:
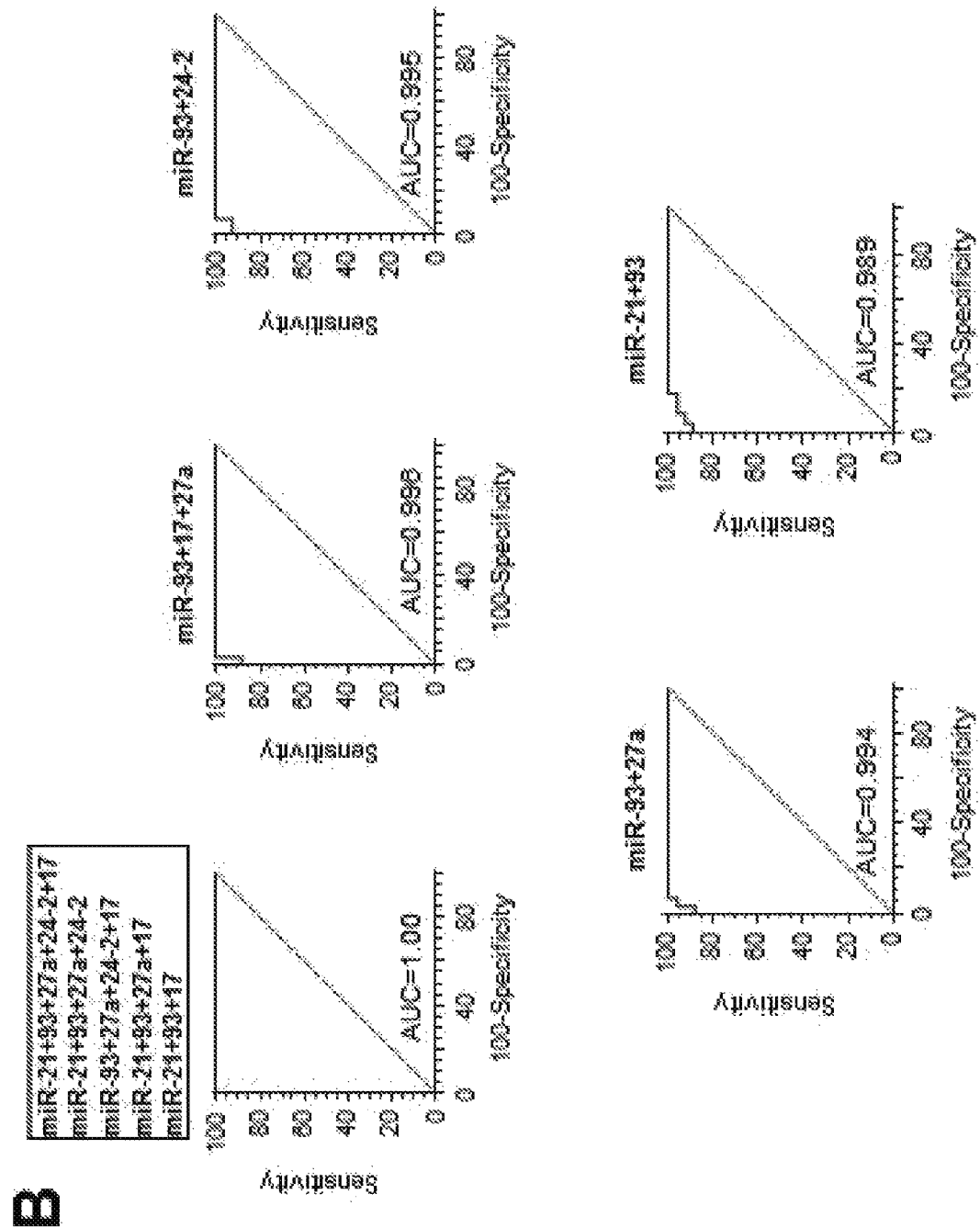
Figure 7C:
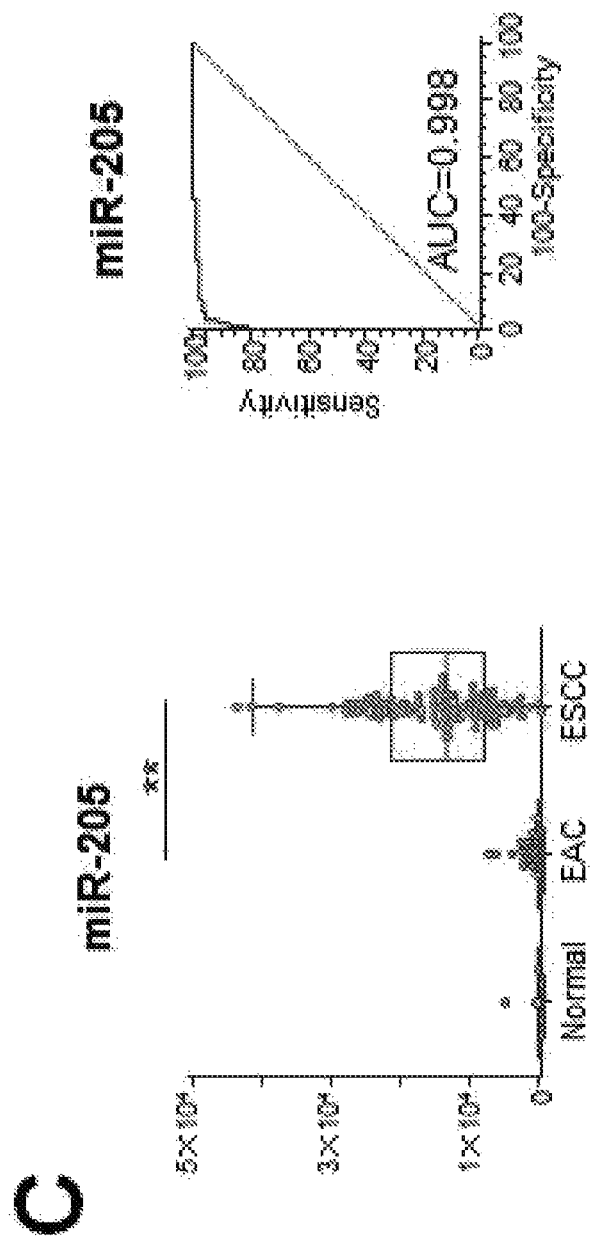
Figure 9:
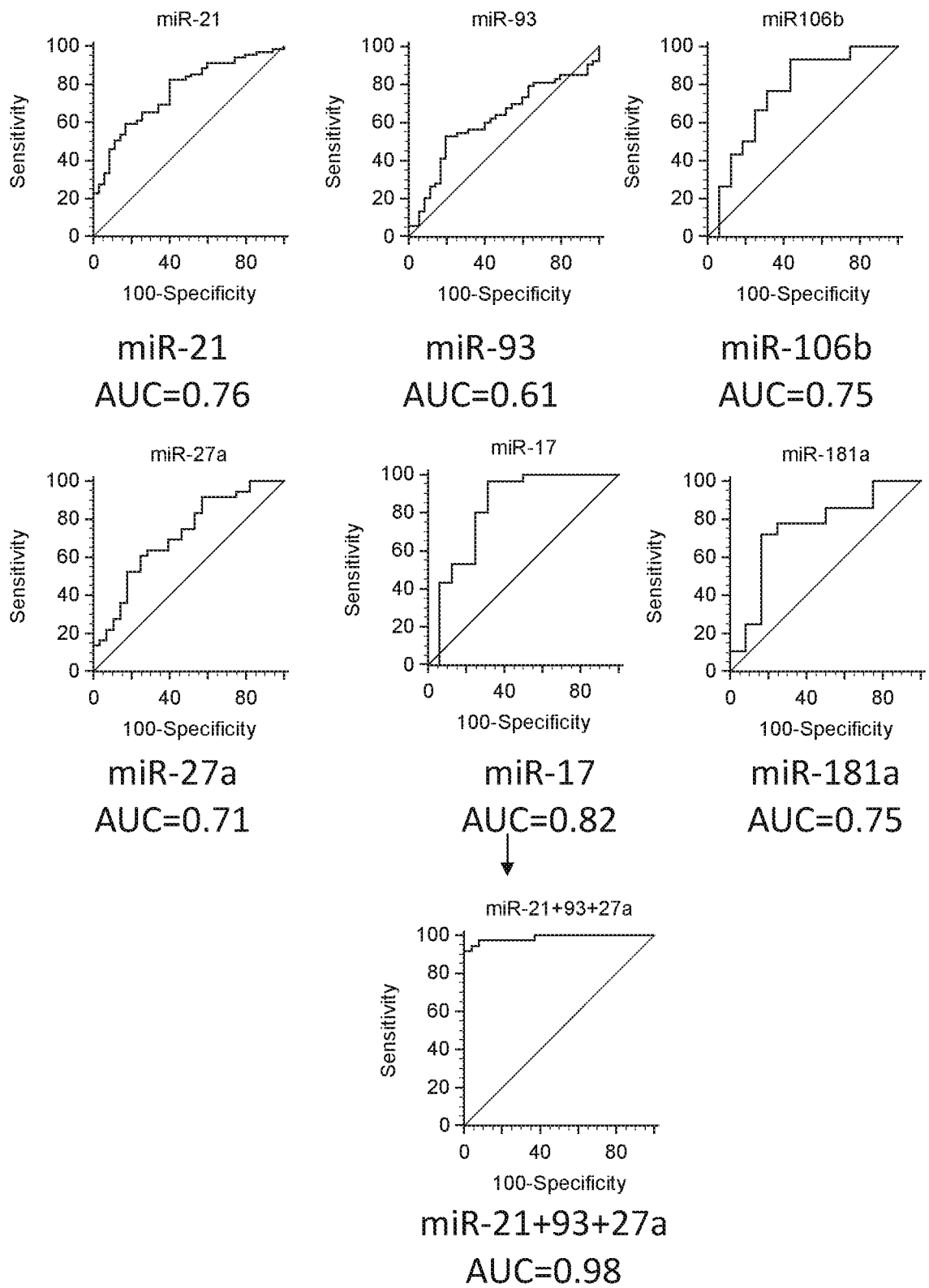
FIG. 9: Serum validation 1: Asia cohort (Nagoya).
Figure 10:
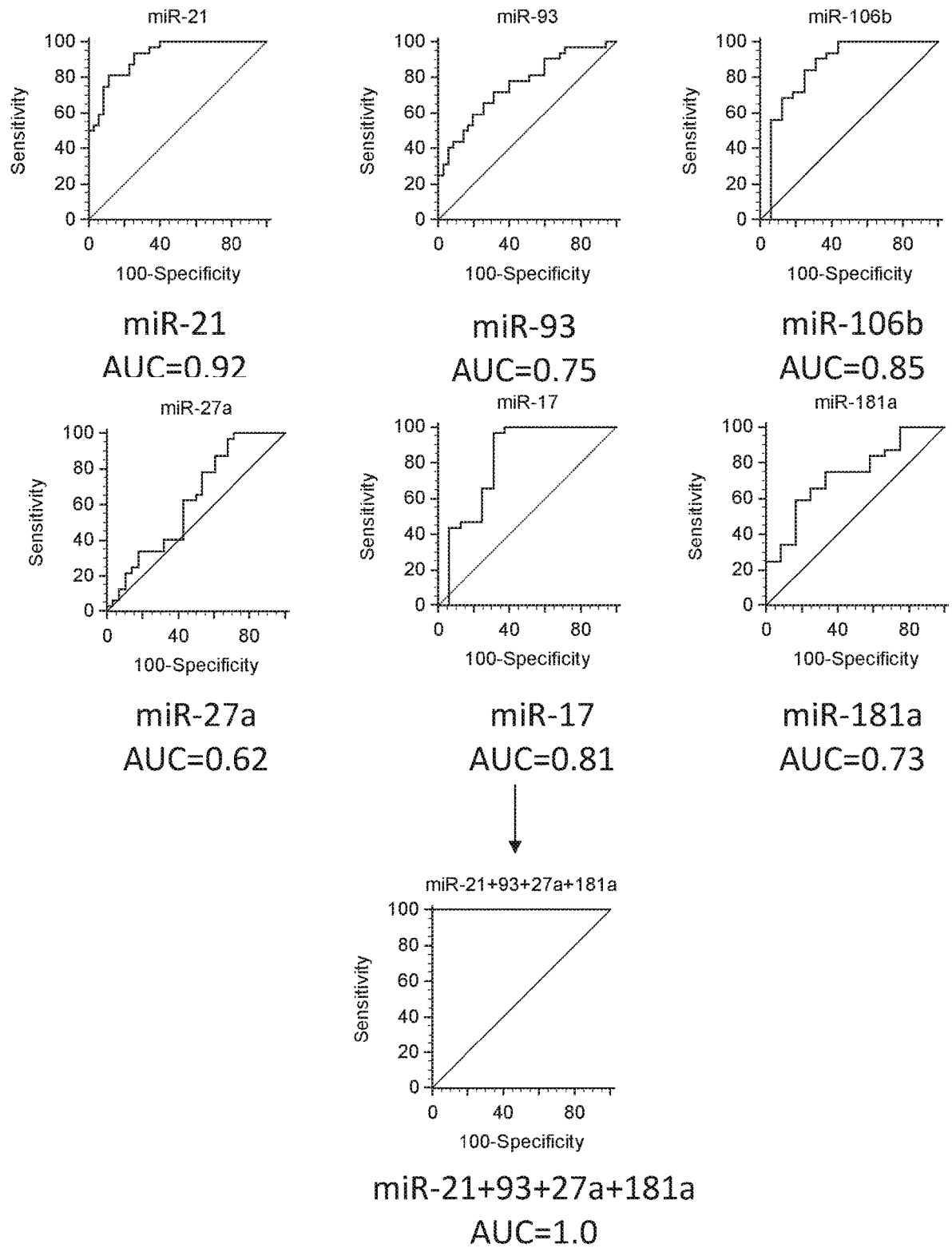
FIG. 10: Serum validation 2: Western cohort (Italy).
Figure 11:
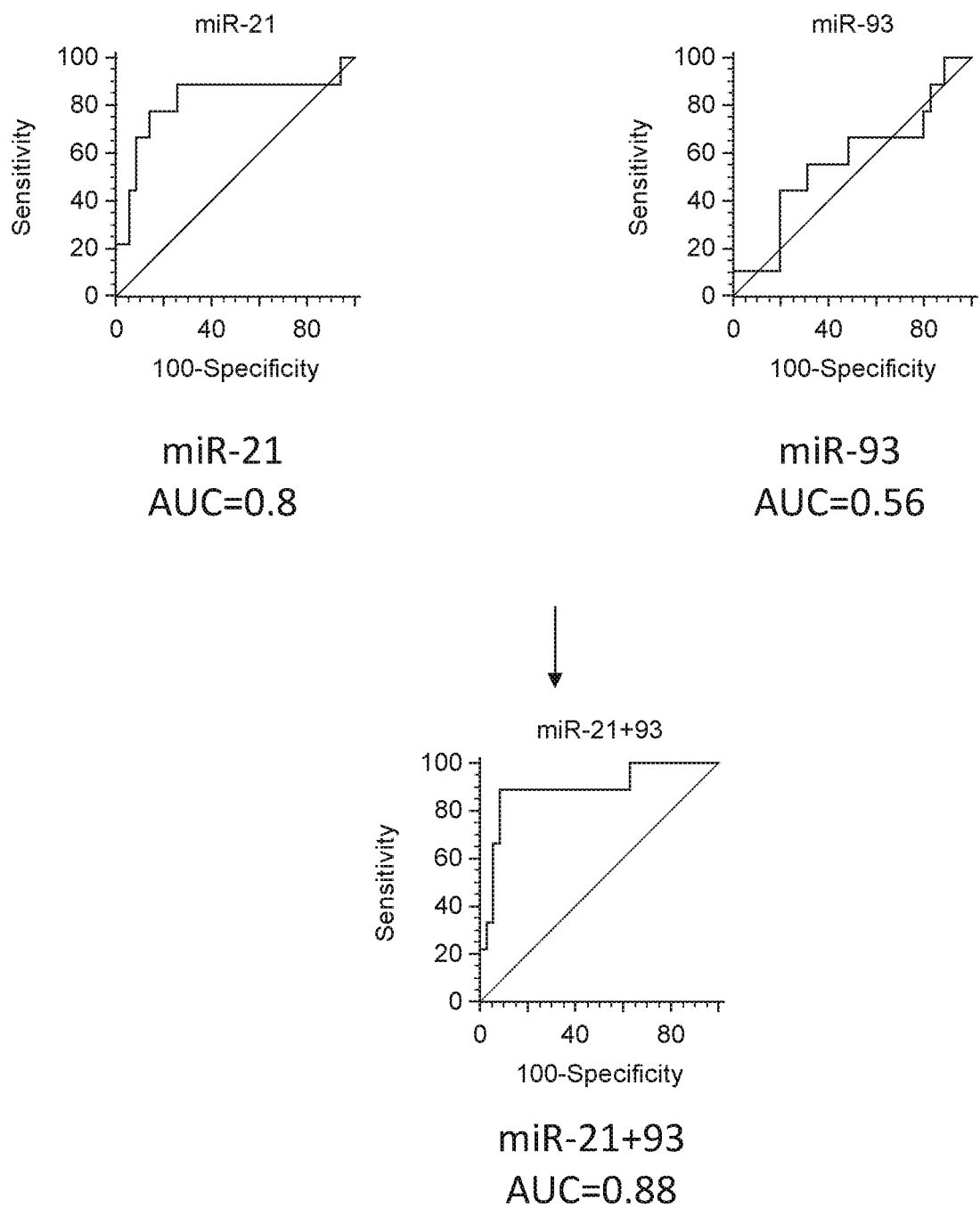
FIG. 11: Serum validation 3: Africa cohort (South Africa).
Figure 12:
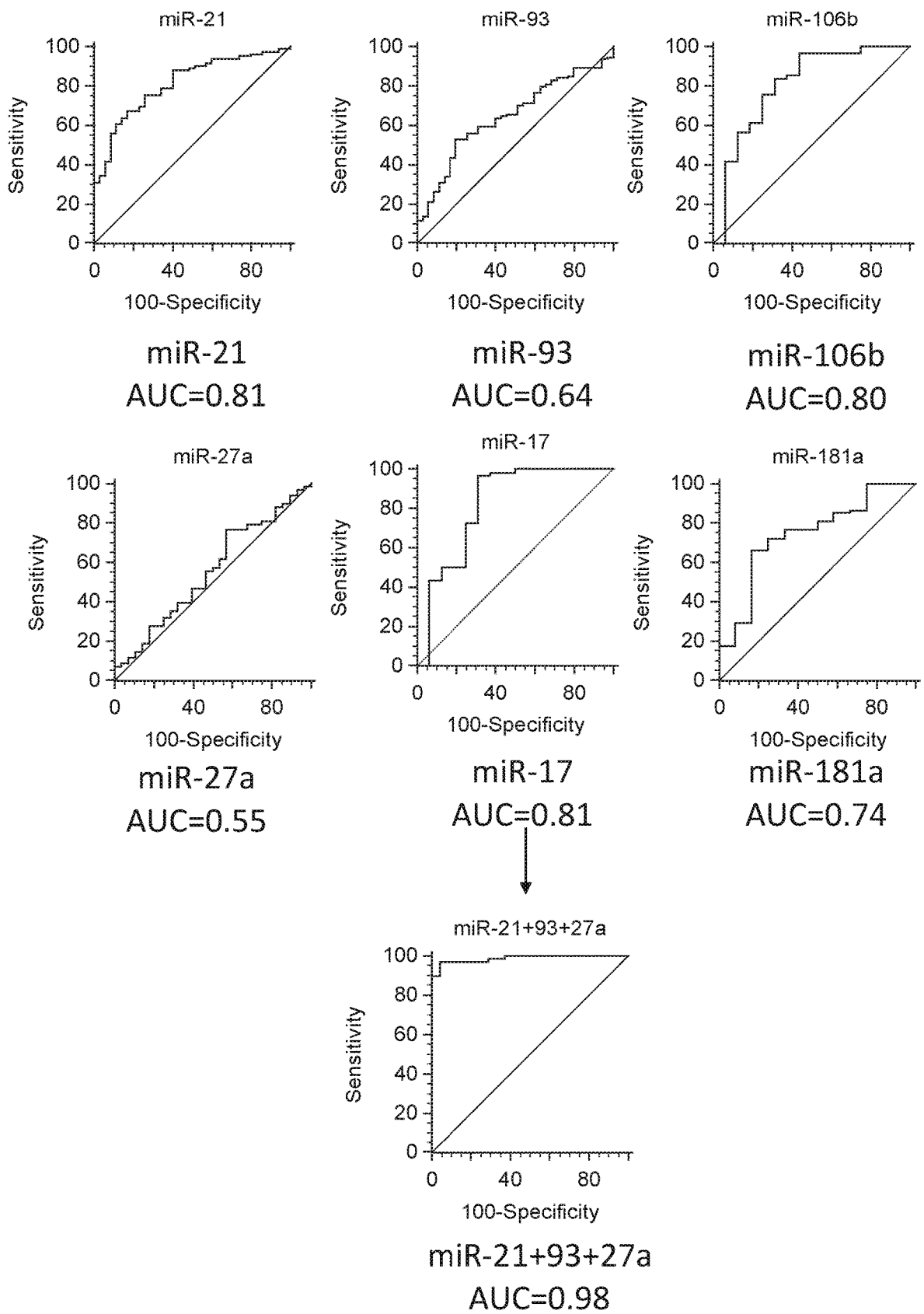
FIG. 12: Serum: Total (Western+Asia+Africa cohort).

Certain aspects of the invention provide a test that could assist physicians to select the optimal therapy for a patient from several alternative treatment options. A major clinical challenge in cancer treatment is to identify the subset of patients who will benefit from a therapeutic regimen, both in metastatic and adjuvant settings. The number of anti-cancer drugs and multi-drug combinations has increased substantially in the past decade, however, treatments continue to be applied empirically using a trial-and-error approach. Here methods and compositions are provided to diagnose patients to determine the optimal treatment option for cancer patients.

I. DEFINITIONS

The term substantially the same or not significantly different refers to a level of expression that is not significantly different than what it is compared to. Alternatively, or in conjunction, the term substantially the same refers to a level of expression that is less than 2, 1.5, or 1.25 fold different than the expression level it is compared to or less than 20, 15, 10, or 5% difference in expression.

By "subject" or "patient" is meant any single subject for which therapy is desired, including humans, cattle, dogs, guinea pigs, rabbits, chickens, and so on. Also intended to be included as a subject are any subjects involved in clinical research trials not showing any clinical sign of disease, or subjects involved in epidemiological studies, or subjects used as controls.

The term "primer," as used herein, is meant to encompass any nucleic acid that is capable of priming the synthesis of a nascent nucleic acid in a template-dependent process. Typically, primers are oligonucleotides from ten to twenty and/or thirty base pairs in length, but longer sequences can be employed. Primers may be provided in double-stranded and/or single-stranded form, although the single-stranded form is preferred.

As used herein, "increased expression" or "elevated expression" or "decreased expression" refers to an expression level of a biomarker in the subject's sample as compared to a reference level representing the same biomarker or a different biomarker. In certain aspects, the reference level may be a reference level of expression from a non-cancerous tissue from the same subject. Alternatively, the reference level may be a reference level of expression from a different subject or group of subjects. For example, the reference level of expression may be an expression level obtained from a sample (e.g., a tissue, fluid or cell sample) of a subject or group of subjects without cancer, or an expression level obtained from a non-cancerous tissue of a subject or group of subjects with cancer. The reference level may be a single value or may be a range of values. The reference level of expression can be determined using any method known to those of ordinary skill in the art. In some embodiments, the reference level is an average level of expression determined from a cohort of subjects with cancer or without cancer. The reference level may also be depicted graphically as an area on a graph. In certain embodiments, a reference level is a normalized level, while in other embodiments, it may be a level that is not stable with respect to the tissue or biological sample being tested.

"About" and "approximately" shall generally mean an acceptable degree of error for the quantity measured given the nature or precision of the measurements. Typically, exemplary degrees of error are within 20 percent (%), preferably within 10%, and more preferably within 5% of a given value or range of values. Alternatively, and particularly in biological systems, the terms "about" and "approximately" may mean values that are within an order of magnitude, preferably within 5-fold and more preferably within 2-fold of a given value. In some embodiments it is contemplated that an numerical value discussed herein may be used with the term "about" or "approximately."

II. MIRNA

Certain aspects are based, in part, on the systematic discovery and validation of miI<NA(s) biomarkers of esophageal cancer. In certain embodiments, microRNAs (herein abbreviated miRNAs miR or mir) may be used in methods and compositions for determining the prognosis, for diagnosing subjects, for determining a response to a particular cancer treatment, of a particular patient, and for treating individuals with esophageal cancer.

MiRNAs may be naturally occurring, small non-coding RNAs that are about 17 to about 25 nucleotide bases (nt) in length in their biologically active form. miRNAs post-transcriptionally regulate gene expression by repressing target mRNA translation. It is thought that miRNAs function as negative regulators, i.e. greater amounts of a specific miRNA will correlate with lower levels of target gene expression.

There may be three forms of miRNAs existing in vivo, primary miRNAs (pri-miRNAs), premature miRNAs (pre-miRNAs), and mature miRNAs. Primary miRNAs (pri-miRNAs) are expressed as stem-loop structured transcripts of about a few hundred bases to over 1 kb. The pri-miRNA transcripts are cleaved in the nucleus by an RNase II endonuclease called Drosha that cleaves both strands of the stem near the base of the stem loop. Drosha cleaves the RNA duplex with staggered cuts, leaving a 5' phosphate and 2 nt overhang at the 3' end.

The cleavage product, the premature miRNA (pre-miRNA) may be about 60 to about 110 nt long with a hairpin structure formed in a fold-back manner. Pre-miRNA is transported from the nucleus to the cytoplasm by Ran-GTP and Exportin-5. Pre-miRNAs are processed further in the cytoplasm by another RNase II endonuclease called Dicer. Dicer recognizes the 5' phosphate and 3' overhang, and cleaves the loop off at the stem-loop junction to form miRNA duplexes. The miRNA duplex binds to the RNA-induced silencing complex (RISC), where the antisense strand is preferentially degraded and the sense strand mature miRNA directs RISC to its target site. It is the mature miRNA that is the biologically active form of the miRNA and is about 17 to about 25 nt in length.

MicroRNAs function by engaging in base pairing (perfect or imperfect) with specific sequences in their target genes' messages (mRNA). The miRNA degrades or represses translation of the mRNA, causing the target genes' expression to be post-transcriptionally down-regulated, repressed, or silenced. In animals, miRNAs do not necessarily have perfect homologies to their target sites, and partial homologies lead to translational repression, whereas in plants, where miRNAs tend to show complete homologies to the target sites, degradation of the message (mRNA) prevails.

MicroRNAs are widely distributed in the genome, dominate gene regulation, and actively participate in many physiological and pathological processes. For example, the regulatory modality of certain miRNAs is found to control cell proliferation, differentiation, and apoptosis; and abnormal miRNA profiles are associated with oncogenesis. Additionally, it is suggested that viral infection causes an increase in miRNAs targeted to silence "pro-cell survival" genes, and a decrease in miRNAs repressing genes associated with apoptosis (programmed cell death), thus tilting the balance toward gaining apoptosis signaling.

In other embodiments of the invention, there are synthetic nucleic acids that are miRNA inhibitors or antagonists. In some embodiments, the miRNA inhibitor or antagonist is an antagomir. A miRNA inhibitor is between about 17 to 25 nucleotides in length and comprises a 5' to 3' sequence that is at least 90% complementary to the 5' to 3' sequence of a mature miRNA. In certain embodiments, a miRNA inhibitor molecule is 17, 18, 19, 20, 21, 22, 23, 24, or 25 nucleotides in length, or any range derivable therein. Moreover, a miRNA inhibitor has a sequence (from 5' to 3') that is or is at least 90, 91, 92, 93, 94, 95, 96, 97, 98, 99, 99.1, 99.2, 99.3, 99.4, 99.5, 99.6, 99.7, 99.8, 99.9 or 100% complementary, or any range derivable therein, to the 5' to 3' sequence of a mature miRNA, particularly a mature, naturally occurring miRNA. One of skill in the art could use a portion of the probe sequence that is complementary to the sequence of a mature miRNA as the sequence for a miRNA inhibitor. Moreover, that portion of the probe sequence can be altered so that it is still 90% complementary to the sequence of a mature miRNA.

In certain embodiments, a synthetic miRNA has one or more modified nucleic acid residues. In certain embodiments, the sugar modification is a 2'O-Me modification, a 2'F modification, a 2'H modification, a 2'amino modification, a 4'ribose modification, or a phosphorothioate modification on the carboxy group linked to the carbon at position 6. In further embodiments, there is one or more sugar modifications in the first or last 2 to 4 residues of the complementary region or the first or last 4 to 6 residues of the complementary region.

Yet further, the nucleic acid structure of the miRNA can also be modified into a locked nucleic acid (LNA) with a methylene bridge between the 2 Oxygen and the 4' carbon to lock the ribose in the 3'-endo (North) conformation in the A-type conformation of nucleic acids (Lennox, et al, 2011; Bader, et al 2011). This modification significantly increases both target specificity and hybridization properties of the molecules.

The miRNA region and the complementary region may be on the same or separate polynucleotides. In cases in which they are contained on or in the same polynucleotide, the miRNA molecule will be considered a single polynucleotide. In embodiments in which the different regions are on separate polynucleotides, the synthetic miRNA will be considered to be comprised of two polynucleotides.

When the RNA molecule is a single polynucleotide, there is a linker region between the miRNA region and the complementary region. In some embodiments, the single polynucleotide is capable of forming a hairpin loop structure as a result of bonding between the miRNA region and the complementary region. The linker constitutes the hairpin loop. It is contemplated that in some embodiments, the linker region is, is at least, or is at most 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, or 40 residues in length, or any range derivable therein. In certain embodiments, the linker is between 3 and 30 residues (inclusive) in length.

In addition to having a miRNA region and a complementary region, there may be flanking sequences as well at either the 5' or 3' end of the region. In some embodiments, there is or is at least 1, 2, 3, 4, 5, 6, 7, 8, 9, 10 nucleotides or more, or any range derivable therein, flanking one or both sides of these regions.

Other miRNA-based therapies that negatively manipulate oncogenic miRNAs', may include further include miRNA sponges, miRNA masks or locked nucleic acid (LNA). As used herein, the term "miRNA sponge" refers to a synthetic nucleic acid (e.g. a mRNA transcript) that contains multiple tandem-binding sites for a miRNA of interest, and that serves to titrate out the endogenous miRNA of interest, thus inhibiting the binding of the miRNA of interest to its endogenous targets.

Methods in certain aspects include reducing, eliminating, or inhibiting activity and/or expression of one or more miRNAs in a cell comprising introducing into a cell a miRNA inhibitor, antagonist, or antagomir; or supplying or enhancing the activity of one or more miRNAs in a cell. Certain embodiments also concern inducing certain cellular characteristics by providing to a cell a particular nucleic acid, such as a specific synthetic miRNA molecule or a synthetic miRNA inhibitor molecule. However, in methods of the invention, the miRNA molecule or miRNA inhibitor need not be synthetic. They may have a sequence that is identical to a naturally occurring miRNA or they may not have any design modifications. In certain embodiments, the miRNA molecule and/or a miRNA inhibitor are synthetic, as discussed above.

III. ESOPHAGEAL CANCER STAGING AND TREATMENTS

Methods and compositions may be provided for treating esophageal cancer with particular applications of miRNA expression levels. Based on a profile of miRNA expression levels, different treatments may be prescribed or recommended for different cancer patients.

Esophageal cancer, also called esophagus cancer, begins in the cells that line the esophagus. Specifically, cancer of the esophagus begins in the inner layer of the esophageal wall and grows outward. If it spreads through the esophageal wall, it can travel to lymph nodes, which are the tiny, bean-shaped organs that help fight infection, as well as the blood vessels in the chest and other nearby organs. Esophageal cancer can also spread to the lungs, liver, stomach, and other parts of the body.

There are two major types of esophageal cancer: esophagus squamous cell carcinoma (ESCC), which starts in squamous cells that line the esophagus, and usually develops in the upper and middle part of the esophagus, and esophagus adenocarcinoma (EAC). This type begins in the glandular tissue in the lower part of the esophagus where the esophagus and the stomach come together.

A. Cancer Staging

The esophageal cancer described herein may be an esophageal cancer of any of the following stages.

1. TNM Staging System

One tool that doctors use to describe the stage is the TNM system. Tumor (T): How deeply has the primary tumor grown into the wall of the esophagus and the surrounding tissue? Node (N): Has the tumor spread to the lymph nodes? If so, where and how many? Metastasis (M): Has the cancer metastasized to other parts of the body? If so, where and how much? There are 5 stages: stage 0 (zero) and stages I through IV (one through four). The following provides more information on the TNM staging system:

Using the TNM system, the "T" plus a letter or number (0 to 4) is used to describe the tumor, including whether the cancer has grown into the wall of the esophagus or nearby tissue, and if so, how deep. Some stages are also divided into smaller groups that help describe the tumor in even more detail. Specific tumor stage information is listed below.

TX: The primary tumor cannot be evaluated.
T0: There is no cancer in the esophagus.
Tis: This is called carcinoma (cancer) in situ. Carcinoma in situ is very early cancer. Cancer cells are in only one small area of the top lining of the esophagus without any spread into the lining.
T1: There is a tumor in the lamina propria and the 2 inside layers of the esophagus called the submucosa. Cancer cells have spread into the lining of the esophagus.
T2: The tumor is in the third layer of the esophagus called the muscularis propria. Cancer cells have spread into but not through the muscle wall of the esophagus.
T3: The tumor is in the outer layer of the esophagus called the adventitia. Cancer cells have spread through the entire muscle wall of the esophagus into surrounding tissue.
T4: The tumor has spread outside the esophagus into areas around it. Cancer cells have spread to structures surrounding the esophagus, including the large blood vessel coming from the heart called the aorta, the windpipe, diaphragm, and the pleural lining of the lung.

The "N" in the TNM staging system stands for lymph nodes. In esophageal cancer, lymph nodes near the esophagus and in the chest are called regional lymph nodes. Lymph nodes in other parts of the body are called distant lymph nodes.

NX: The lymph nodes cannot be evaluated.
N0: The cancer was not found in any lymph nodes.
N1: The cancer has spread to 1 or 2 lymph nodes in the chest, near the tumor.
N2: The cancer has spread to 3 to 6 lymph nodes in the chest, near the tumor.
N3: The cancer has spread to 7 or more lymph nodes in the chest, near the tumor.

The "M" in the TNM system indicates whether the cancer has spread to other parts of the body.

MX: Metastasis cannot be evaluated.
M0: The cancer has not spread to other parts of the body.
M1: The cancer has spread to another part of the body.

2. Grade (G)

Esophageal cancer can also be described by its grade (G), which describes how much cancer cells look like healthy cells when viewed under a microscope. The doctor compares the cancerous tissue with healthy tissue. Healthy tissue usually contains many different types of cells grouped together. If the cancer looks similar to healthy tissue and contains different cell groupings, it is called differentiated or a low-grade tumor. If the cancerous tissue looks very different from healthy tissue, it is called poorly differentiated or a high-grade tumor. The cancer's grade may help the doctor predict how quickly the cancer will spread. In general, the lower the tumor's grade, the better the prognosis.

G1: The tissue looks more like healthy cells — called well differentiated.
G2: The cells are somewhat different than healthy cells — called somewhat differentiated.
G3: The tumor cells barely look like healthy cells — called poorly differentiated.
G4: The cancer cells look almost alike and do not look like healthy cells — called not differentiated.

3. Cancer Stage Grouping

Doctors assign the stage of the cancer by combining the T, N, and M classifications. There are separate staging systems for the two most common types of esophageal cancer: squamous cell carcinoma and adenocarcinoma. The staging system for each is described below.

a. Staging of Squamous Cell Carcinoma of the Esophagus

In addition to the TNM classifications, for squamous cell carcinoma, the stages may be subdivided based on whether the tumor is located in the upper, middle, or lower section of the esophagus, as well as the grade (G) of the tumor cells.

| Stage | Description |
|---|---|
| Stage 0 | This is the same as Tis cancer, in which cancer is found in only the top lining of the esophagus (Tis, N0, M0, G1). |
| Stage IA | This is the same as T1 cancer, in which the cancer is located in only the 2 inside layers of the esophagus (T1, N0, M0, G1). |
| Stage IB | Either of these conditions:<br>The cancer is located in only the 2 inside layers of the esophagus, but the tumor cells are less differentiated (T1, N0, M0, G2 or G3).<br>The tumor is located in the lower part of the esophagus, and the cancer has spread to either of the 2 outer layers of the esophagus, but not to the lymph nodes or other parts of the body (T2 or T3, N0, M0, G1). |
| Stage IIA | Either of these conditions:<br>The tumor is located in the upper or middle part of the esophagus, and the cancer is in either of the 2 outer layers of the esophagus (T2 or T3, N0, M0, G1).<br>The tumor is located in the lower part of the esophagus, and the cancer is in either of the 2 outer layers of the esophagus. The tumor cells are less differentiated (T2 or T3, N0, M0, G2 or G3). |
| Stage IIB | Either of these conditions:<br>The tumor is located in the upper or middle part of the esophagus, and cancer is in either of the 2 outer layers of the esophagus. The tumor cells are less differentiated (T2 or T3, N0, M0, G2 or G3).<br>Cancer is in the inner layers of the esophagus and has spread to 1 or 2 lymph nodes near the tumor (T1 or T2, N1, M0, any G). |
| Stage IIIA | Any of these conditions:<br>Cancer is in the inner layers of the esophagus and has spread to 3 to 6 lymph nodes near the tumor (T1 or T2, N2, M0, any G).<br>Cancer is in the outside layer of the esophagus and has spread to 1 or 2 lymph nodes (T3, N1, M0, any G).<br>Cancer has spread beyond the esophagus to nearby tissue but not to lymph nodes or other areas of the body (T4a, N0, M0, any G). |
| Stage IIIB | Cancer is in the outside layer of the esophagus and in 3 to 6 lymph nodes (T3, N2, M0, any G). |
| Stage IIIC | Any of these conditions:<br>Cancer has spread beyond the esophagus into nearby tissue. Cancer is also in 6 or less lymph nodes (T4a, N1 or N2, M0, any G).<br>Cancer has spread beyond the esophagus into nearby tissue and cannot be removed by surgery (T4b, any N, M0, any G).<br>Cancer has spread to 7 or more lymph nodes but not to distant parts of the body (any T, N3, M0, any G). |
| Stage IV | Cancer has spread to another part of the body (any T, any N, M1, any G). | b. Staging of Adenocarcinoma of the Esophagus

For adenocarcinoma, doctors use the T, N, and M classifications, as well as the grade (G).

| | |
|---|---|
| Stage 0 | This is the same as Tis cancer, in which cancer is found in only the top lining of the esophagus (Tis, N0, M0, G1). |
| Stage IA | This is the same as T1 cancer, in which the cancer is located in either of the 2 inside layers of the esophagus only (T1, N0, M0, G1 or G2). |
| Stage IB | Either of these conditions:<br>The cancer is located in either of the 2 inside layers of the esophagus only, and the tumor cells are poorly differentiated (T1, N0, M0, G3).<br>The cancer has spread to an outer layer of the esophagus but not to the lymph nodes or other parts of the body (T2, N0, M0, G1 or G2). |
| Stage IIA | Cancer is in an outer layer of the esophagus, and the cells are poorly differentiated (T2, N0, M0, G3). |
| Stage IIB | Either of these conditions:<br>Cancer is in the outside layer of the esophagus but not beyond (T3, N0, M0, any G).<br>Cancer is in an inner layer or the muscularis propria of the esophagus and has spread to 1 or two lymph nodes (T1 or T2, N1, M0, any G). |
| Stage IIIA | Any of these conditions:<br>Cancer is in the inner layers of the esophagus and has spread to 3 to 6 lymph nodes near the tumor (T1 or T2, N2, M0, any G).<br>Cancer is in the outside layer of the esophagus and has spread to 1 or 2 lymph nodes (T3, N1, M0, any G).<br>Cancer has spread beyond the esophagus to nearby tissue but not to lymph nodes or other areas of the body (T4a, N0, M0, any G). |
| Stage IIIB | Cancer is in the outside layer of the esophagus and in 3 to 6 lymph nodes (T3, N2, M0, any G). |
| Stage IIIC | Any of these conditions:<br>Cancer has spread beyond the esophagus into nearby tissue. Cancer is also in 6 or less lymph nodes (T4a, N1 or N2, M0, any G).<br>Cancer has spread beyond the esophagus into nearby tissue and cannot be removed by surgery (T4b, any N, M0, any G).<br>Cancer has spread to 7 or more lymph nodes but not to distant parts of the body (any T, N3, M0, any G). |
| Stage IV | Cancer has spread to another part of the body (any T, any N, M1, any G). |

Recurrent cancer is cancer that has come back after treatment. It may come back in the esophagus or in another part of the body. If the cancer does return, there will be another round of tests to learn about the extent of the recurrence. These tests and scans are often similar to those done at the time of the original diagnosis.

B. Therapy

The following treatment steps/active ingredients are useful in the methods described herein. It is also contemplated that the following treatment steps/therapeutic agents may be specifically excluded in the embodiments described herein. For people with a tumor that has not spread beyond the esophagus and lymph nodes, it is often recommend combining different types of treatment: radiation therapy, chemotherapy, and surgery. The order of treatments varies, and several factors are considered, including the type of esophageal cancer.

Particularly for squamous cell cancer, chemotherapy and radiation therapy, a combination called chemoradiotherapy, are commonly recommended as the first treatment, with surgery afterwards depending how well chemoradiotherapy worked. Recent studies show using chemoradiotherapy before surgery is better than surgery alone.

For adenocarcinoma, the most common treatment in the United States is chemotherapy and radiation therapy followed by surgery. Surgery is almost always recommended after chemoradiotherapy, unless there are factors that increase the risks from surgery, such as a patient's age or overall health.

For advanced esophageal cancer, treatment usually involves chemotherapy and radiation therapy.

Cancer and its treatment often cause side effects. In addition to treatment to slow, stop, or eliminate the cancer, an important part of cancer care is relieving a person's symptoms and side effects. This approach is called palliative or supportive care, and it includes supporting the patient with his or her physical, emotional, and social needs.

Palliative care is any treatment that focuses on reducing symptoms, improving quality of life, and supporting patients and their families. Any person, regardless of age or type and stage of cancer, may receive palliative care. It works best when palliative care is started as early as needed in the cancer treatment process. People often receive treatment for the cancer and treatment to ease side effects at the same time. In fact, patients who receive both often have less severe symptoms, better quality of life, and report they are more satisfied with treatment.

Palliative treatments vary widely and often include medication, nutritional changes, relaxation techniques, emotional support, and other therapies. Palliative treatments may also include those similar to those meant to eliminate the cancer, such as chemotherapy, surgery, or radiation therapy.

1. Surgery

Surgery is the removal of the tumor and some surrounding healthy tissue during an operation. A surgical oncologist is a doctor who specializes in treating cancer using surgery. Surgery has traditionally been the most common treatment for esophageal cancer. However, currently, surgery is used as the main treatment only for patients with early-stage esophageal cancer.

For patients with locally-advanced esophageal cancer, a combination of chemotherapy and radiation therapy (see below) may be used before surgery to shrink the tumor. For people who cannot have surgery, the best treatment option is often a combination of chemotherapy and radiation therapy.

The most common surgery to treat esophageal cancer is called an esophagectomy, where the doctor removes the affected part of the esophagus and then connects the remaining healthy part of the esophagus to the stomach so that the patient can swallow normally. The stomach or part of the intestine may sometimes be used to make the connection. The surgeon also removes lymph nodes around the esophagus.

In addition to surgery to treat the disease, surgery may be used to help patients eat and relieve symptoms caused by the cancer. This is called palliative surgery. To do this, surgeons and gastroenterologists can:

1.) put in a percutaneous gastrostomy or jejunostomy, also called a feeding tube, so that a person can receive nutrition directly into the stomach or intestine. This may be done before chemotherapy and radiation therapy is given to make sure that the patient can eat enough food to maintain his or her weight and strength during treatment; or 2.) create a bypass, or new pathway, to the stomach if a tumor blocks the esophagus but cannot be removed with surgery; this procedure is rarely used.

People who have had trouble eating and drinking may need intravenous (IV; into a vein) feedings and fluids for several days before and after surgery, as well as antibiotics to prevent or treat infections. Patients learn special coughing and breathing exercises to keep their lungs clear.

2. Endoscopic Therapy

The following treatments use an endoscope (see Diagnosis) to treat esophageal cancer and to manage side effects caused by the tumor. Endoscopy and dilation is a procedure that expands the esophagus. It may have to be repeated if the tumor grows. Endoscopy with stent placement is a procedure that uses an endoscopy to insert a stent in the esophagus. An esophageal stent is a metal, mesh device that is expanded to keep the esophagus open.

Photodynamic therapy is a palliative or supportive care option used to make swallowing easier, especially for people who cannot or choose not to have surgery, radiation therapy, or chemotherapy. In photodynamic therapy, a light-sensitive substance is injected into the tumor and stays longer in cancer cells than in healthy cells. A light is then aimed at the tumor, destroying the cancer cells. Although photodynamic therapy may relieve swallowing problems for a short period of time, it does not cure esophageal cancer.

Electrocoagulation is a type of palliative treatment helps kill cancer cells by heating them with an electric current. This is sometimes used to help relieve symptoms by removing a blockage caused by the tumor.

Cryotherapy is a type of palliative treatment that uses an endoscope with a probe attached that can freeze and remove tumor tissue. It can be used to reduce the size of a tumor to help a patient swallow better.

3. Radiation Therapy

Radiation therapy is the use of high-energy x-rays or other particles to destroy cancer cells. A radiation therapy regimen (schedule) usually consists of a specific number of treatments given over a set period of time. The most common type of radiation treatment is called external-beam radiation therapy, which is radiation therapy given from a machine outside the body. When radiation treatment is given directly inside the body, it is called internal radiation therapy or brachytherapy. For esophageal cancer, this involves temporarily inserting a radioactive wire into the esophagus using an endoscope.

4. Chemotherapy

Chemotherapy and radiotherapy for esophageal cancer may be delivered preoperatively, postoperatively, or independent of surgery. Most chemotherapy that is currently used for the treatment of esophageal cancer include alkylating, antimetabolite, anthracycline, and antimicrotubular agents. Chemotherapy for squamous cell esophageal carcinoma, as with squamous cell carcinomas in general, may be based on cisplatin.

In some embodiments, chemoradiotherapy is administered, followed by surgery. In some embodiments, neoadjuvant therapy is used. In some embodiments, neoadjuvant therapy comprises a combination of radiotherapy and chemotherapy with a platinum compound and a DNA replication inhibitor. In some embodiments, the platinum compound is selected from cisplatin, carboplatin, oxaliplatin, nedaplatin, triplatin tetranitrate, phenathriplatin, picoplatin, and satraplatin. In some embodiments, the platinum compound is cisplatin. In some embodiments, the DNA replication inhibitor is 5-fluorouracil.

In some embodiments, the chemotherapy comprises carboplatin, paclitaxel, cisplatin, 5-fluorouracil, epirubicin, docetaxel, cepecitabine, oxaliplatin, and combinations thereof. In some embodiments, the combination treatment comprises carboplatin and paclitaxel; cisplatin and 5-fluorouracil; epirubicin, cisplatin, and 5-fluorouracil; docetaxel, cisplatin, and 5-fluorouracil; cisplatin and cepacitabine; oxaliplatin and 5-fluorouracil; and oxaliplatin and capecitabine.

5. Targeted Therapy

Targeted therapy is a treatment that targets the cancer's specific genes, proteins, or the tissue environment that contributes to cancer growth and survival. This type of treatment blocks the growth and spread of cancer cells while limiting damage to healthy cells.

For esophageal cancer, the targeted therapy trastuzumab (Herceptin) may be used along with chemotherapy for patients with metastatic esophageal adenocarcinoma. Trastuzumab targets a protein called human epidermal growth receptor 2 (HER2). About 20% to 30% of esophageal adenocarcinomas make too much HER2.

The targeted therapy ramucirumab (Cyramza) is also an option after first-line therapy, or the first treatments given, has not worked. It may be given by itself or with paclitaxel (Taxol), a type of chemotherapy.

C. Monitoring

In certain aspects, the biomarker-based method may be combined with one or more other esophageal cancer diagnosis or screening tests at increased frequency if the patient is determined to be at high risk for recurrence or have a poor prognosis.

The esophagus monitoring may include any methods known in the art. In particular, the monitoring include obtaining a sample and testing the sample for diagnosis. For example, the monitoring may include endoscopy of the esophagus and/or biopsy. Other monitoring test include imaging tests, barium swallow tests, CAT scan (computed tomography scan), magnetic resonance imaging (MRI) scan, positron emission tomography (PET) scan, endoscopy such as upper endoscopy, endoscopic ultrasound, bronchoscopy, thoracoscopy, laparoscopy, or combinations thereof.

In further aspects, the monitoring diagnosis may include lab tests such as HER2 testing of biopsy samples, a complete blood count (CBC) blood test to look for anemia, a check of a stool sample for occult blood, and/or blood tests to check for normal kidney or liver function.

IV. ROC ANALYSIS

In statistics, a receiver operating characteristic (ROC), or ROC curve, is a graphical plot that illustrates the performance of a binary classifier system as its discrimination threshold is varied. The curve is created by plotting the true positive rate against the false positive rate at various threshold settings. (The true-positive rate is also known as sensitivity in biomedical informatics, or recall in machine learning. The false-positive rate is also known as the fall-out and can be calculated as 1−specificity). The ROC curve is thus the sensitivity as a function of fall-out. In general, if the probability distributions for both detection and false alarm are known, the ROC curve can be generated by plotting the cumulative distribution function (area under the probability distribution from −infinity to +infinity) of the detection probability in the y-axis versus the cumulative distribution function of the false-alarm probability in x-axis.

ROC analysis provides tools to select possibly optimal models and to discard suboptimal ones independently from (and prior to specifying) the cost context or the class distribution. ROC analysis is related in a direct and natural way to cost/benefit analysis of diagnostic decision making.

The ROC is also known as a relative operating characteristic curve, because it is a comparison of two operating characteristics (TPR and FPR) as the criterion changes. ROC analysis curves are known in the art and described in Metz C E (1978) Basic principles of ROC analysis. Seminars in Nuclear Medicine 8:283-298; Youden W J (1950) An index for rating diagnostic tests. Cancer 3:32-35; Zweig M H, Campbell G (1993) Receiver-operating characteristic (ROC) plots: a fundamental evaluation tool in clinical medicine. Clinical Chemistry 39:561-577; and Greiner M, Pfeiffer D, Smith R D (2000) Principles and practical application of the receiver-operating characteristic analysis for diagnostic tests. Preventive Veterinary Medicine 45:23-41, which are herein incorporated by reference in their entirety.

V. SAMPLE PREPARATION

In certain aspects, methods involve obtaining a sample from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from esophageal tissue by any of the biopsy methods previously mentioned. In other embodiments the sample may be obtained from any of the tissues provided herein that include but are not limited to non-cancerous or cancerous tissue and non-cancerous or cancerous tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be obtained by methods known in the art. In certain embodiments the samples are obtained by biopsy. In other embodiments the sample is obtained by swabbing, endoscopy, scraping, phlebotomy, or any other methods known in the art. In some cases, the sample may be obtained, stored, or transported using components of a kit of the present methods. In some cases, multiple samples, such as multiple esophageal samples may be obtained for diagnosis by the methods described herein. In other cases, multiple samples, such as one or more samples from one tissue type (for example esophagus) and one or more samples from another specimen (for example serum) may be obtained for diagnosis by the methods. In some cases, multiple samples such as one or more samples from one tissue type (e.g. esophagus) and one or more samples from another specimen (e.g. serum) may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, endoscopy, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a esophageal or a suspected esophageal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided.

In some embodiments, the subject may be referred to a specialist such as an oncologist, surgeon, or endocrinologist.

The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

VI. NUCLEIC ACID ASSAYS

Aspects of the methods include assaying nucleic acids to determine expression levels. Arrays can be used to detect differences between two samples. Specifically contemplated applications include identifying and/or quantifying differences between miRNA from a sample that is normal and from a sample that is not normal, between a cancerous condition and a non-cancerous condition, or between two differently treated samples. Also, miRNA may be compared between a sample believed to be susceptible to a particular disease or condition and one believed to be not susceptible or resistant to that disease or condition. A sample that is not normal is one exhibiting phenotypic trait(s) of a disease or condition or one believed to be not normal with respect to that disease or condition. It may be compared to a cell that is normal with respect to that disease or condition. Phenotypic traits include symptoms of, or susceptibility to, a disease or condition of which a component is or may or may not be genetic or caused by a hyperproliferative or neoplastic cell or cells.

An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, which are hereby incorporated in their entirety for all purposes.

In addition to the use of arrays and microarrays, it is contemplated that a number of difference assays could be employed to analyze miRNAs, their activities, and their effects. Such assays include, but are not limited to, nucleic amplification, polymerase chain reaction, quantitative PCR, RT-PCR, in situ hybridization, Northern hybridization, hybridization protection assay (HPA)(GenProbe), branched DNA (bDNA) assay (Chiron), rolling circle amplification (RCA), single molecule hybridization detection (US Genomics), Invader assay (ThirdWave Technologies), and/or Bridge Litigation Assay (Genaco).

VII. PHARMACEUTICAL COMPOSITIONS

In certain aspects, the compositions or agents for use in the methods, such as chemotherapeutic agents, are suitably contained in a pharmaceutically acceptable carrier. The carrier is non-toxic, biocompatible and is selected so as not to detrimentally affect the biological activity of the agent. The agents in some aspects of the invention may be formulated into preparations for local delivery (i.e. to a specific location of the body, such as skeletal muscle or other tissue) or systemic delivery, in solid, semi-solid, gel, liquid or gaseous forms such as tablets, capsules, powders, granules, ointments, solutions, depositories, inhalants and injections allowing for oral, parenteral or surgical administration. Certain aspects of the invention also contemplate local administration of the compositions by coating medical devices and the like.

Suitable carriers for parenteral delivery via injectable, infusion or irrigation and topical delivery include distilled water, physiological phosphate-buffered saline, normal or lactated Ringer's solutions, dextrose solution, Hank's solution, or propanediol. In addition, sterile, fixed oils may be employed as a solvent or suspending medium. For this purpose any biocompatible oil may be employed including synthetic mono- or diglycerides. In addition, fatty acids such as oleic acid find use in the preparation of injectables. The carrier and agent may be compounded as a liquid, suspension, polymerizable or non-polymerizable gel, paste or salve.

The carrier may also comprise a delivery vehicle to sustain (i.e., extend, delay or regulate) the delivery of the agent(s) or to enhance the delivery, uptake, stability or pharmacokinetics of the therapeutic agent(s). Such a delivery vehicle may include, by way of non-limiting examples, microparticles, microspheres, nanospheres or nanoparticles composed of proteins, liposomes, carbohydrates, synthetic organic compounds, inorganic compounds, polymeric or copolymeric hydrogels and polymeric micelles.

In certain aspects, the actual dosage amount of a composition administered to a patient or subject can be determined by physical and physiological factors such as body weight, severity of condition, the type of disease being treated, previous or concurrent therapeutic interventions, idiopathy of the patient and on the route of administration. The practitioner responsible for administration will, in any event, determine the concentration of active ingredient(s) in a composition and appropriate dose(s) for the individual subject.

In certain embodiments, pharmaceutical compositions may comprise, for example, at least about 0.1% of an active agent, such as an isolated exosome, a related lipid nanovesicle, or an exosome or nanovesicle loaded with therapeutic agents or diagnostic agents. In other embodiments, the active agent may comprise between about 2% to about 75% of the weight of the unit, or between about 25% to about 60%, for example, and any range derivable therein. In other non-limiting examples, a dose may also comprise from about 1 microgram/kg/body weight, about 5 microgram/kg/body weight, about 10 microgram/kg/body weight, about 50 microgram/kg/body weight, about 100 microgram/kg/body weight, about 200 microgram/kg/body weight, about 350 microgram/kg/body weight, about 500 microgram/kg/body weight, about 1 milligram/kg/body weight, about 5 milligram/kg/body weight, about 10 milligram/kg/body weight, about 50 milligram/kg/body weight, about 100 milligram/kg/body weight, about 200 milligram/kg/body weight, about 350 milligram/kg/body weight, about 500 milligram/kg/body weight, to about 1000 mg/kg/body weight or more per administration, and any range derivable therein. In non-limiting examples of a derivable range from the numbers listed herein, a range of about 5 microgram/kg/body weight to about 100 mg/kg/body weight, about 5 microgram/kg/body weight to about 500 milligram/kg/body weight, etc., can be administered.

Solutions of pharmaceutical compositions can be prepared in water suitably mixed with a surfactant, such as hydroxypropylcellulose. Dispersions also can be prepared in glycerol, liquid polyethylene glycols, mixtures thereof and in oils. Under ordinary conditions of storage and use, these preparations contain a preservative to prevent the growth of microorganisms.

In certain aspects, the pharmaceutical compositions are advantageously administered in the form of injectable compositions either as liquid solutions or suspensions; solid forms suitable for solution in, or suspension in, liquid prior to injection may also be prepared. These preparations also may be emulsified. A typical composition for such purpose comprises a pharmaceutically acceptable carrier. For instance, the composition may contain 10 mg or less, 25 mg, 50 mg or up to about 100 mg of human serum albumin per milliliter of phosphate buffered saline. Other pharmaceutically acceptable carriers include aqueous solutions, non-toxic excipients, including salts, preservatives, buffers and the like.

Examples of non-aqueous solvents are propylene glycol, polyethylene glycol, vegetable oil and injectable organic esters such as ethyloleate. Aqueous carriers include water, alcoholic/aqueous solutions, saline solutions, parenteral vehicles such as sodium chloride, Ringer's dextrose, etc. Intravenous vehicles include fluid and nutrient replenishers. Preservatives include antimicrobial agents, antifungal agents, anti-oxidants, chelating agents and inert gases. The pH and exact concentration of the various components the pharmaceutical composition are adjusted according to well-known parameters.

Additional formulations are suitable for oral administration. Oral formulations include such typical excipients as, for example, pharmaceutical grades of mannitol, lactose, starch, magnesium stearate, sodium saccharine, cellulose, magnesium carbonate and the like. The compositions take the form of solutions, suspensions, tablets, pills, capsules, sustained release formulations or powders.

In further aspects, the pharmaceutical compositions may include classic pharmaceutical preparations. Administration of pharmaceutical compositions according to certain aspects may be via any common route so long as the target tissue is available via that route. This may include oral, nasal, buccal, rectal, vaginal or topical. Topical administration may be particularly advantageous for the treatment of skin cancers, to prevent chemotherapy-induced alopecia or other dermal hyperproliferative disorder. Alternatively, administration may be by orthotopic, intradermal, subcutaneous, intramuscular, intraperitoneal or intravenous injection. Such compositions would normally be administered as pharmaceutically acceptable compositions that include physiologically acceptable carriers, buffers or other excipients. For treatment of conditions of the lungs, aerosol delivery can be used. Volume of the aerosol is between about 0.01 ml and 0.5 ml.

An effective amount of the pharmaceutical composition is determined based on the intended goal. The term "unit dose" or "dosage" refers to physically discrete units suitable for use in a subject, each unit containing a predetermined-quantity of the pharmaceutical composition calculated to produce the desired responses discussed above in association with its administration, i.e., the appropriate route and treatment regimen. The quantity to be administered, both according to number of treatments and unit dose, depends on the protection or effect desired.

Precise amounts of the pharmaceutical composition also depend on the judgment of the practitioner and are peculiar to each individual. Factors affecting the dose include the physical and clinical state of the patient, the route of administration, the intended goal of treatment (e.g., alleviation of symptoms versus cure) and the potency, stability and toxicity of the particular therapeutic substance.

VIII. KITS

Certain aspects of the present invention also concern kits containing compositions of the invention or compositions to implement methods of the invention. In some embodiments, kits can be used to evaluate one or more miRNA molecules. In certain embodiments, a kit contains, contains at least or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more miRNA probes, synthetic miRNA molecules or miRNA inhibitors, or any value or range and combination derivable therein. In some embodiments, there are kits for evaluating miRNA activity in a cell.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

Kits for using miRNA probes, synthetic miRNAs, non-synthetic miRNAs, and/or miRNA inhibitors of the invention for prognostic or diagnostic applications are included as part of the invention. Specifically contemplated are any such molecules corresponding to any miRNA identified herein.

In certain aspects, negative and/or positive control synthetic miRNAs and/or miRNA inhibitors are included in some kit embodiments. The control molecules can be used to verify transfection efficiency and/or control for transfection-induced changes in cells.

It is contemplated that any method or composition described herein can be implemented with respect to any other method or composition described herein and that different embodiments may be combined. It is specifically contemplated that any methods and compositions discussed herein with respect to miRNA molecules or miRNA may be implemented with respect to synthetic miRNAs to the extent the synthetic miRNA is exposed to the proper conditions to allow it to become a mature miRNA under physiological circumstances. The claims originally filed are contemplated to cover claims that are multiply dependent on any filed claim or combination of filed claims.

Any embodiment of the invention involving specific miRNAs by name is contemplated also to cover embodiments involving miRNAs whose sequences are at least 80, 81, 82, 83, 84, 85, 86, 87, 88, 89, 90, 91, 92, 93, 94, 95, 96, 97, 98, 99% identical to the mature sequence of the specified miRNA.

Embodiments of the invention include kits for analysis of a pathological sample by assessing miRNA profile for a sample comprising, in suitable container means, two or more miRNA probes, wherein the miRNA probes detect one or more of the miRNA identified herein. The kit can further comprise reagents for labeling miRNA in the sample. The kit may also include labeling reagents, including at least one of amine-modified nucleotide, poly(A) polymerase, and poly (A) polymerase buffer. Labeling reagents can include an amine-reactive dye.

IX. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

The following methods were implemented in collecting the data provided in the figures of the application.
A. Study Design and Clinical Specimens
This study consisted of three parts: a discovery phase for candidate miRNA panel selection, the validation phase, and the translation phase. The final phase aimed to evaluate the potentiality of miRNA panel in the serum in esophageal cancer patients. In the discovery phase, the inventors used the cohort of 186 stage I-IV esophageal cancer tissues that included 98 esophagus squamous-cell carcinoma tissues and 88 esophagus adenocarcinoma tissues, and 12 normal mucosal tissues from The Cancer Genome Atlas (TCGA) data. The expression data of miRNAs and the corresponding clinical data for esophageal cancer patients were downloaded from The Cancer Genome Atlas data portal. There were 27 female and 157 male patients with age 66.1±11.8 and 61.8±11.7 years, respectively. The collection of the original material and data of TCGA was conducted in compliance with all applicable laws, regulations and policies for the protection of human subjects, and necessary IRB approvals were obtained. Data are summarized either as mean with 95% confidence intervals on the log scale, or these value were exponentiated to generate fold-change. The validation phase included 224 stage 0-IV esophageal cancer tissues and 224 matched corresponding normal esophageal mucosal tissues. The translation phase included 136 stage 0-IV esophageal cancer patients and 112 healthy controls to examine serum levels of miRNAs. A total of 224 esophageal cancer tissues and 224 matched corresponding normal esophageal mucosal tissues and 136 serum samples from stage 0-IV at Nagoya University Medical Hospital, Japan and 112 healthy controls at Baylor University Medical Center, TX, US were used in this study. Written informed consent was obtained from all patients, and the study was approved by the institutional review boards of all participating institutions.
B. RNA Isolation from Tissues and qRT-PCR
Total RNA including small RNA was isolated from tissues using the RNeasy Mini Kit (Qiagen, Valencia, Calif.) according to the manufacturer's protocol and eluted in 30 μL of RNase-free water using QIAcube devise (Qiagen, Valencia, Calif.) and quantified using a NanoDrop spectrophotometer (NanoDrop Technologies, Wilmington, Del.). For miRNA-based RT-PCR assays, 2 μL of enriched small RNAs from tissue samples were reverse-transcribed using the TaqMan MicroRNA Reverse Transcriotion Kit (Applied Biosystems, San Diego, Calif.) in a total reaction volume of 10 μL with the following conditions: 16° C. for 30 min, 42° C. for 30 min, 85° C. for 5 min and maintain at 4° C. Real-time PCR was conducted using MicroRNA Assay Kits and TaqMan Universal Master Mix II, no UNG (Applied Biosystems). PCR reactions for quantification of miRNAs was performed using a QuantStudio 6 Flex Real-Time PCR System (Applied Biosystems) with the following cycling conditions: 95° C. for 10 min, followed by 40 cycles of 95° C. for 15 seconds and 60° C. for 1 min. Results were expressed as $2^{-\Delta\Delta ct}$, and the results were normalized to RNU6B (Applied Biosystems) and performed in duplicate.
C. RNA Isolation from Serum and qRT-PCR
Small RNAs were enriched from all serum samples using the Qiagen miRNAeasy Serum/Plasma Kit (Qiagen, Valencia, Calif.). Briefly, 250 μL of serum was thawed on ice and centrifuged at 10,000 rpm for 5 minutes to remove cellular debris. Next, 200 μL of supernatant was lysed in 1000 μL of Qiazol Lysis Reagent. For normalization of sample-to-sample variation during the RNA isolation procedures, 25 fmol of synthetic *C. elegans* miRNA (cel-miR-39) was added to each denatured sample. Total RNA including small RNA was extracted and eluted in 30 μL of RNase-free water using QIAcube devise (Qiagen, Valencia, Calif.). For miRNA-based RT-PCR assays, 2 μL of enriched small RNAs from serum samples were reverse-transcribed using the TaqMan MicroRNA Reverse Transcriotion Kit (Applied Biosystems, San Diego, Calif.) in a total reaction volume of 10 μL with the following conditions: 16° C. for 30 min, 42° C. for 30 min, 85° C. and maintain at 4° C. Real-time PCR was conducted using MicroRNA Assay Kits and TaqMan Universal Master Mix II, no UNG (Applied Biosystems). PCR reactions for quantification of miRNAs was performed using a QuantStudio 6 Flex Real-Time PCR System (Applied Biosystems) with the following cycling conditions: 95° C. for 10 min, followed by 40 cycles of 95° C. for 15 seconds and 60° C. for 1 min. Results were expressed as $2^{-\Delta\Delta ct}$, and the results were normalized to cel-miR-39 and performed in duplicate
D. Statistical Analysis
To evaluate significant differences between two matched pair groups or between two independent groups of samples, paired t test and Mann-Whitney U test were used, respectively. All P-values were two-sided and a P-value of <0.05 was considered significant. Receiver operating characteristic (ROC) curve were generated and the area under the ROC curve (AUC) with 95% confidence intervals (CI) were computed to assess the discriminating performance of miRNAs. Logistic regression was used for analyzing a dataset in which there are one or more independent variables that determine an outcome. All statistical analysis was performed using the Medcalc statistical software v.12.7.7. (Medcalc Software bvba, Ostend, Belgium).

The table below shows candidate mRNAs for EAC or ESCC-specific markers and their percentages.

| EAC top 10 by using random forrest | % | ESCC top 10 by using random forrest | % |
|---|---|---|---|
| hsa-mir-196a-1 | 100 | hsa-mir-205 | 100 |
| hsa-mir-196b | 100 | hsa-mir-944 | 100 |
| mir-21 | 100 | hsa-mir-194-2 | 98 |
| mir-181a-1 | 96 | hsa-mir-192 | 92 |
| hsa-mir-196a-2 | 96 | hsa-mir-194-1 | 88 |
| hsa-mir-335 | 92 | hsa-mir-23a | 80 |
| hsa-mir-181b-1 | 70 | mir-215 | 74 |
| hsa-mir-15b | 48 | hsa-mir-27a | 74 |

-continued

| EAC top 10 by using random forrest | % | ESCC top 10 by using random forrest | % |
|---|---|---|---|
| hsa-mir-17 | 44 | hsa-mir-338 | 64 |
| mir-106b | 38 | mir-21 | 62 |

The table below shows candidate mRNAs for EAC/ESCC markers and their percentages.

| EAC/ESCC combined top 15 by using random forrest miRNA | % | EAC/ESCC combined top 15 by using t.test miRNA | % |
|---|---|---|---|
| mir-146b | 100 | mir-21 | 64 |
| mir-148a | 100 | mir-93 | 54 |
| mir-181a-1 | 100 | hsa-mir-196a-1 | 52 |
| hsa-mir-196a-1 | 100 | mir-106b | 44 |
| hsa-mir-196b | 100 | hsa-mir-27a | 42 |
| mir-21 | 100 | hsa-mir-1468 | 38 |
| hsa-mir-196a-2 | 84 | mir-139 | 32 |
| hsa-mir-181b-1 | 82 | hsa-mir-196b | 32 |
| hsa-mir-375 | 66 | hsa-mir-17 | 30 |
| hsa-mir-3648 | 54 | hsa-mir-196a-2 | 30 |
| hsa-mir-18a | 48 | mir-181a-1 | 28 |
| hsa-mir-27a | 48 | hsa-mir-421 | 28 |
| has-mir-129-2 | 46 | hsa-mir-181b-1 | 26 |
| has-mir-769 | 40 | hsa-mir-224 | 24 |
| has-mir-106b | 36 | hsa-mir-24-2 | 24 |

Example 2: A Novel miRNA-Based, Non-Invasive, Diagnostic Panel for Detection of Esophageal Squamous Cell Carcinoma As described in this example, a comprehensive in silico analysis was used to identify candidate miRNAs overexpressed in ESCC. Subsequently these miRNAs were tested in serum samples and refined to the 8-miRNA diagnostic panel. The robustness of the panel was validated in two large independent cohorts. Furthermore, panel distinguished early stage ESCC patients from healthy controls, and was significantly superior to currently used serological ESCC marker, SCC-Ag.

Despite esophageal squamous cell carcinoma (ESCC) accounts for almost 80% of all esophageal cancers, currently there is no established serological molecular marker for its early diagnosis. The objective of this study was to establish a circulating miRNA-based diagnostic panel for ESCC through systematic and comprehensive miRNA expression analysis in multiple independent ESCC patient cohorts. Three tissue RNA-Seq datasets were used to identify initial miRNA candidates, and the expression of these candidate miRNAs was validated in clinical tissue samples. Using age, sex, and race-matched serum samples from ESCC patients against those of healthy controls, the inventors mathematically developed a circulating miRNA-panel. Two independent patient cohorts were used assess the diagnostic performance of the miRNA panel. Initially 18 consistently overexpressed miRNAs were identified in three datasets. Subsequently, the expression of these miRNAs was validated in clinical tissue samples. The expression of these tissue-candidates was assessed in serum specimens, and an 8-miRNA panel (miR-103, 106b, 151, 17, 181a, 21, 25, and 93) was employed to derive a multivariate risk scoring formula. The diagnostic performance of the miRNA signature was demonstrated in both the training cohort (AUC=0.83) and two large independent validation cohorts (AUC: 0.80, 0.89, respectively). Furthermore, the miRNA panel distinguished early stage ESCC patients (stage I) from healthy controls (AUC=0.81), which was superior (p-value=0.02) to a clinical serological marker, SCC-Ag (AUC=0.63). Using an integrative comprehensive biomarker discovery and validation approach in potentially the largest cohort of ESCC patients analyzed to date, the inventors have developed and validated a novel and robust miRNA-based panel for the early detection of ESCC.

A. Materials and Methods

1. Data Source

ESCC small RNA-Seq dataset and the corresponding clinical data was downloaded from The Cancer Genome Atlas (TCGA) data portal. TCGA dataset contained 98 stage I-IV ESCC tissues and 13 normal esophageal mucosa. ESCC miRNA microarray datasets were obtained from Gene Expression Omnibus (GEO) with accession codes GSE55856 (108 stage I-IV ESCC tissues and 108 adjacent normal esophageal tissues) and GSE43732 (119 stage I-IV ESCC tissues and 119 adjacent normal esophageal tissues). Affymetrix Multispecies miRNA 2.0 array platform (Affymetrix, Santa Clara, Calif., USA) was used for GSE55856, and the Agilent-038166 cbc Human miRNA18.0 Microarray platform (Agilent Technologies, Palo Alto, Calif.) was used for GSE43732.

2. Clinical Specimens

A total of 863 clinical specimens were collected between 2001 and 2016, including 559 ESCC serum samples, 240 healthy serum samples, 32 ESCC tissue samples, and 32 adjacent normal esophageal mucosa. For tissue validation, 32 stage I-III ESCC tissues and 32 matched corresponding normal esophageal mucosal tissues were collected from patients undergoing esophageal resection for ESCC without any preoperative therapy. First, for the serum refining cohort, 50 stage I-III ESCC serum samples and 50 healthy controls were collected from the Kumamoto University Hospital, Kumamoto in Japan between 2009 and 2011. Next, for the serum training cohort, the inventors collected 280 stage I-IV ESCC serum samples and 128 healthy subjects from Groote Schuur Hospital, Cape Town in South Africa between 2001 and 2015. Finally, the inventors collected the serum validation cohort 1 includes 106 stage I-III ESCC serum samples and 20 healthy controls collected from the Kumamoto University Hospital between 2012 and 2016, and the serum validation cohort 2, includes 123 stage I-III ESCC serum samples and 42 healthy controls collected from the Nagoya University Hospital, Nagoya in Japan between 2001 and 2015. All the procedures were approved by Institutional Review Boards of each hospital and written informed consent was taken from each participant. Whole blood sample of each participant was collected before treatment and subjected at 3000 g for 10 min within 12 h after collection. Then, cell-free serum was further resolved by centrifugation at 10,000 g for 2 min to guarantee complete removal of cell debris. The serum sample was stored in an RNase-free eppendorf tube at −80° C. until use.

3. Study Design

The study design (FIG. 16) includes the following steps: (1) In silico discovery phase. Three tissue-based miRNA expression datasets (TCGA, GSE55856, GSE43732) were used for discovery of a robust miRNA panel. For each dataset significantly overexpressed miRNAs were first identified from each dataset (criteria: log 2 fold-change>0.5, FDR-adjusted p-value<0.05, upregulated in ESCC, AUC>0.7, and the average miRNA expression levels must be >median of all differentially expressed miRNAs). 18 miRNAs that are commonly identified in the three datasets were selected as candidate miRNAs. (2) Tissue validation phase. The expression levels of the 18 candidate miRNAs were evaluated in 32 ESCC tissue samples and 32 matched adjacent normal tissues by qRT-PCR. All candidate miRNAs were confirmed to be significantly upregulated (p-value<0.05) in ESCC tissue samples. (3) Serum refining phase. To develop a diagnostic miRNA panel, the inventors assessed the expression levels of the 18 candidate miRNAs in serum using the serum refining cohort including age, sex, and race matched 50 ESCC patients and 50 healthy controls. Eight miRNAs were found significantly upregulated (p-value<0.05) in ESCC serum samples, and were selected for the following analysis. (4) Serum training and validation phase. Subsequently, we employed multivariate logistic regression to establish an risk scoring formula for ESCC diagnosis using the serum training cohort involving 280 ESCC patients and 128 healthy controls from Groote Schuur Hospital, South Africa. Furthermore, the inventors validated the diagnostic value of the 8-miRNA panel using serum validation cohort 1 (106 ESCC patients and 20 healthy controls from the Kumamoto University Hospital) and serum validation cohort 2 (123 ESCC patients and 42 healthy controls from the Nagoya University Hospital). Using the miRNA signature model, the inventors evaluated the diagnostic performance on the training, validation 1, and validation 2 cohorts by means of sensitivity, specificity, area under the curve (AUC), and corresponding 95% confidence intervals. For all serum cohorts, the risk score is calculated using logistic function $1/(1+\exp(-\text{linear predictors}))$, and the cutoff is the Youden's index of the training cohort: 0.582. The inventors also tested the predictive performance of ESCC by including serum SCC-Ag in serum validation cohort 2.

4. RNA Isolation from Tissues

Total RNA including small RNA was isolated from tissues using the RNeasy Mini Kit (Qiagen, Valencia, Calif.) according to the manufacturer's protocol and eluted in 30 μL of RNase-free water using QIAcube semiautomated robotic devise (Qiagen, Valencia, Calif.) and quantified using a NanoDrop spectrophotometer (NanoDrop Technologies, Wilmington, Del.) and stored at −80° C. for further use.

5. RNA Isolation from Serum

Small RNAs were enriched from all serum samples using the Qiagen miRNAeasy Serum/Plasma Kit (Qiagen). Briefly, serum samples were thawed on ice and centrifuged at 10,000 rpm for 5 minutes to remove cellular debris. Next, 200 μL of supernatant was lysed in 1000 μL of Qiazol Lysis Reagent. For normalization of sample-to-sample variation during the RNA isolation procedures, 25 fmol of synthetic *C. elegans* miRNA (cel-miR-39, Qiagen) was added to each denatured sample. Total RNA including small RNA was extracted and eluted in 30 μL of RNase-free water using QIAcube semiautomated robotic devise (Qiagen) and stored at −80° C. for further use.

6. Quantitative Reverse Transcription Polymerase Chain Reaction (qRT-PCR)

For miRNA-based RT-PCR assays, 1.2 μL of enriched small RNAs from tissue/serum samples were reverse-transcribed using the TaqMan MicroRNA Reverse Transcription Kit (Applied Biosystems) in a total reaction volume of 6 μL with the following conditions: 16° C. for 30 min, 42° C. for 30 min, 85° C. and maintain at 4° C. Real-time PCR was conducted using MicroRNA Assay Kits and TaqMan Universal Master Mix II, no UNG (Applied Biosystems). PCR reactions for quantification of miRNAs was performed using a QuantStudio 6 Flex Real-Time PCR System (Applied Biosystems) with the following cycling conditions: 95° C. for 10 min, followed by 40 cycles of 95° C. for 15 seconds and 60° C. for 1 min. Results were expressed as $\lambda^{-\Delta\Delta ct}$. In tissue specimens, the results were normalized to U6 (Ambion, Austin, Tex.) and in serum specimens, the results were normalized to an internal endogenous control miR-16.

7. Statistical Analysis

To quantify the statistical significance of differential miRNA expression between two matched pair groups or between two independent groups of samples, paired t test and two-sided student's t-test were used, respectively. All p-values were two-sided and a p-value of <0.05 was considered significant. Receiver operating characteristic (ROC) curve were generated and the area under the ROC curve (AUC) with 95% confidence intervals (CI) were computed to assess the discriminative performance of miRNAs. For ESCC diagnosis, a multivariate logistic regression model was trained to predict cancer risk based on the expression levels of the 8 signature miRNAs. All statistical analysis was performed using the Medcalc statistical software (v.12.7.7., Medcalc Software bvba, Ostend, Belgium), JMP software (10.0.2., SAS Institute, Cary, N.C., USA) and R (3.3.3, R Development Core Team, https://cran.r-project.org/).

B. Results

1. Characteristics of Subjects

ESCC serum samples included all pretreatment samples taken before surgery for patients with resectable tumors (n=538) and before chemotherapy for patients with unresectable tumors (n=21). In addition, total 240 serum samples were obtained from healthy controls. There were no significant differences in the distribution of age and there were no significant racial and sex differences between ESCC patients and healthy controls in serum refining cohort, serum training cohort, and serum validation cohort 1 and due to restrictions in the sampling of healthy participants, there was a significant difference in age between patients with ESCC and healthy participants in the serum validation cohort 2 (mean difference, 26.7 years [95% CI, 26.4-28.9 years]).

2. Identification of ESCC Associated miRNA Panel Candidates

Figure 13A:
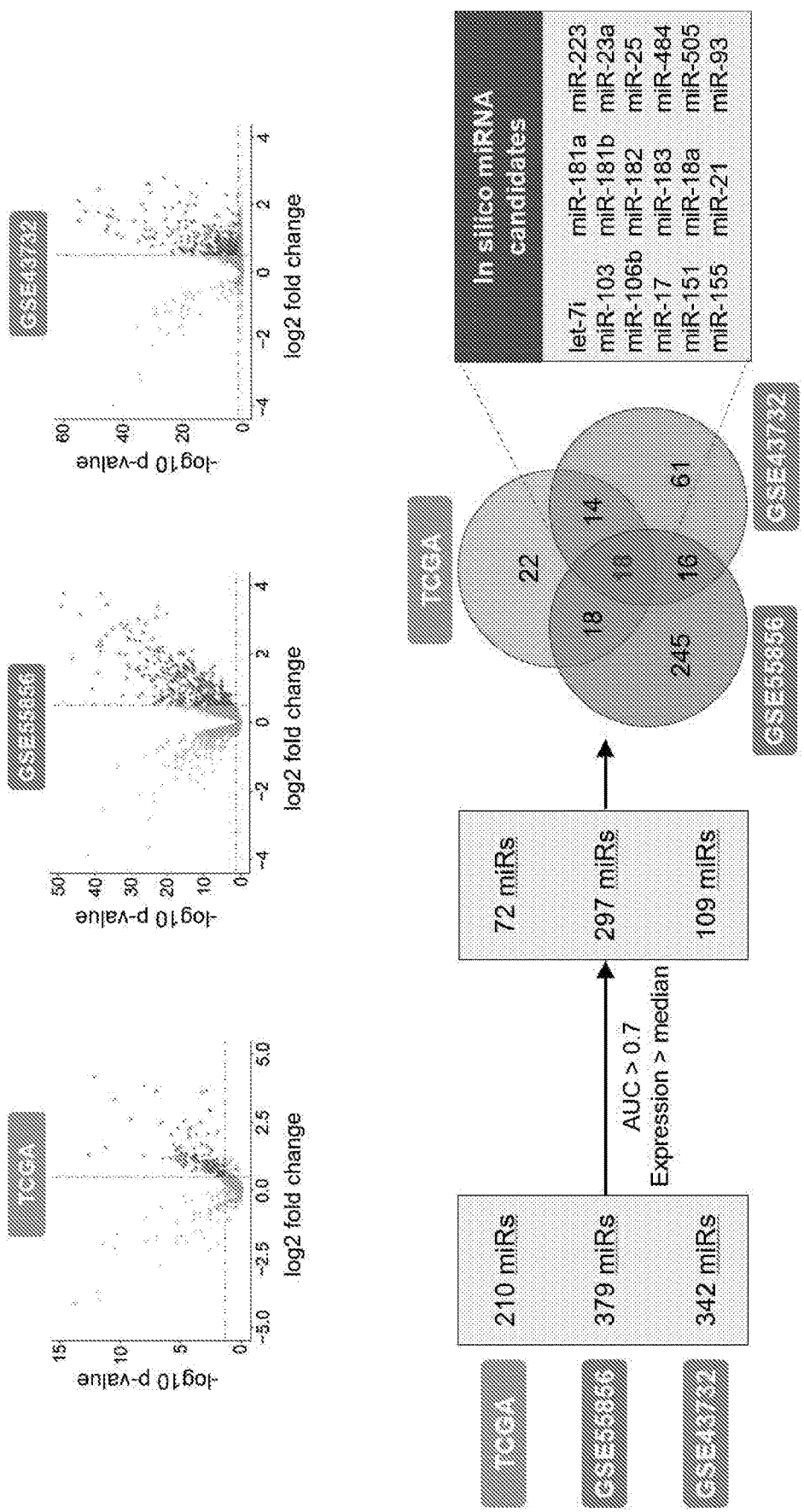
FIG. 13A-B: In silico discovery for Identification of ESCC associated miRNA candidates in tissue. A) In silico miRNA candidates selection for the identification of upregulated miRNAs in ESCC tissue by using three miRNAs expression datasets (TCGA, GSE55856, GSE43732). 18 miRNAs were overlapped between three datasets. B) Heat map of 18 candidate miRNAs for three miRNAs expression datasets. A combination panel of 18 miRNAs was able to accurately distinguished cancer tissues from normal tissues for three datasets (AUC=0.98, 0.99, 0.98, respectively) using repeated 2-fold cross-validation, repeated 100 times.
Figure 13B:
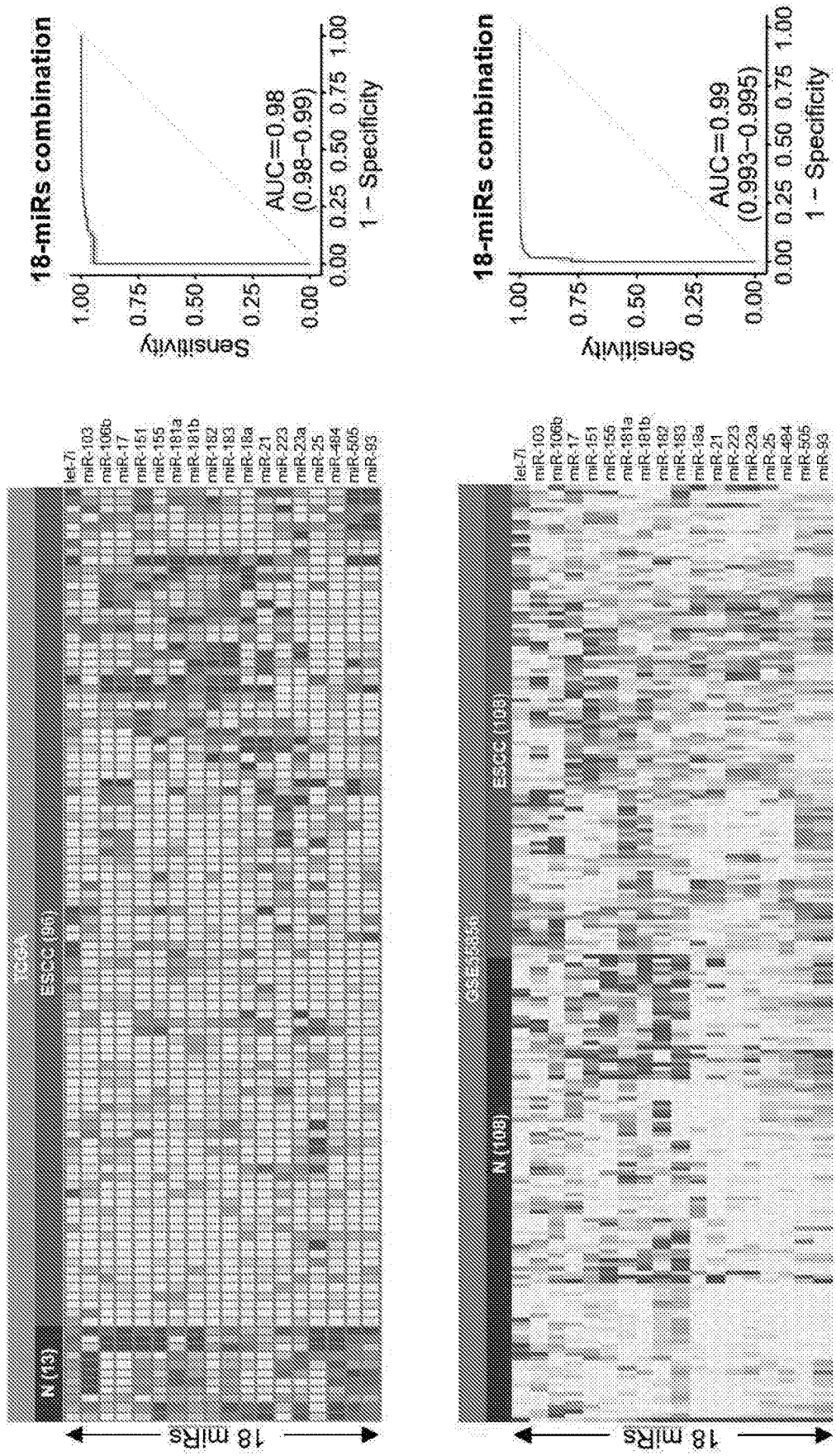
Figure 13B:
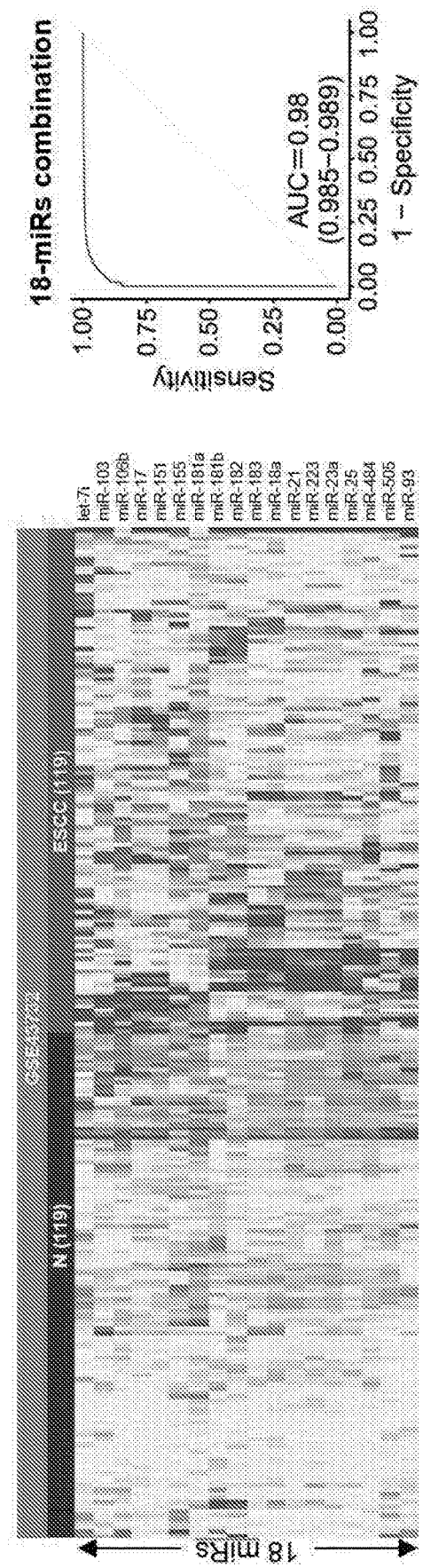
Figure 16:
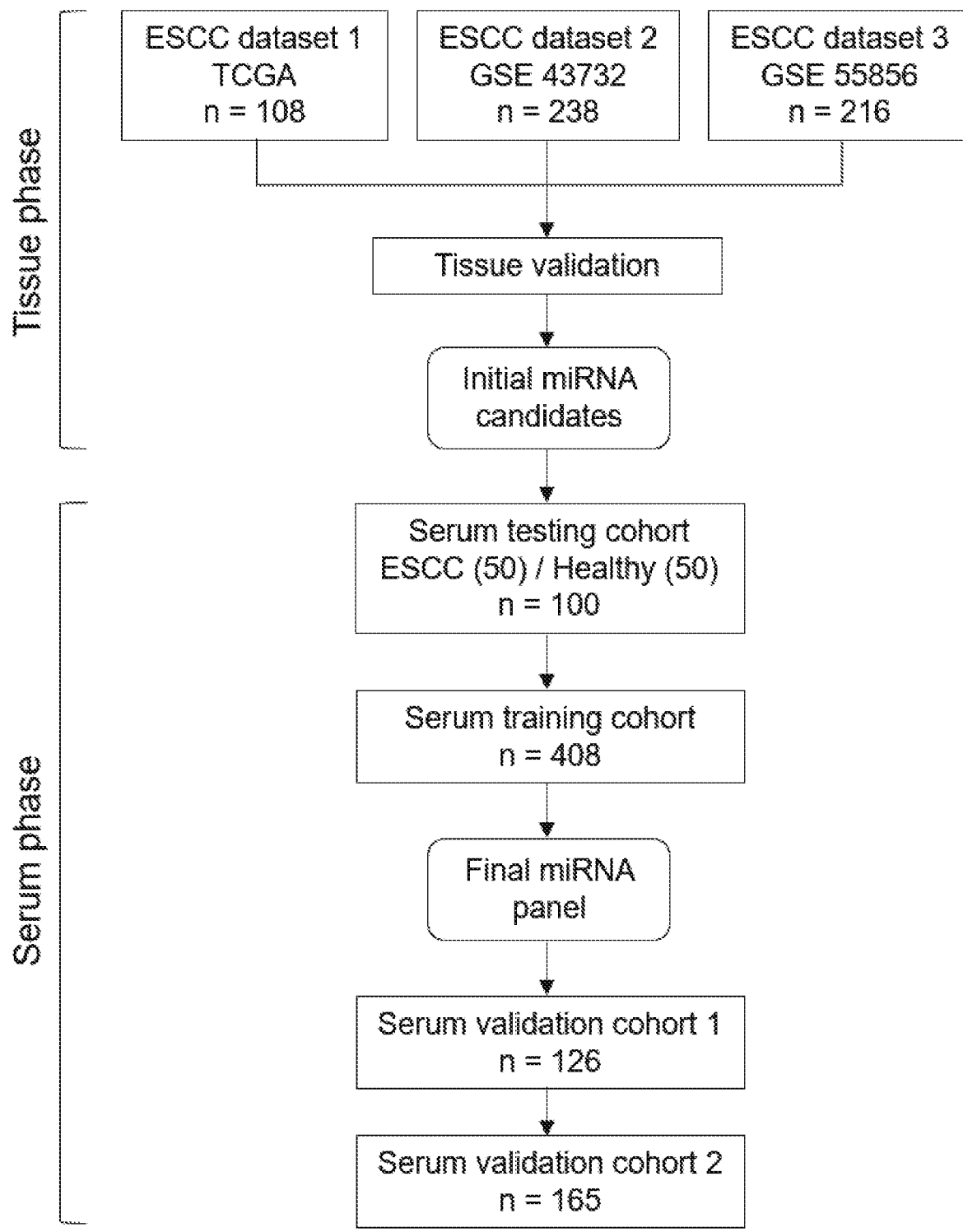
FIG. 16: Study design for the identification of the circulating miRNA panel for ESCC detection.
Figure 17:
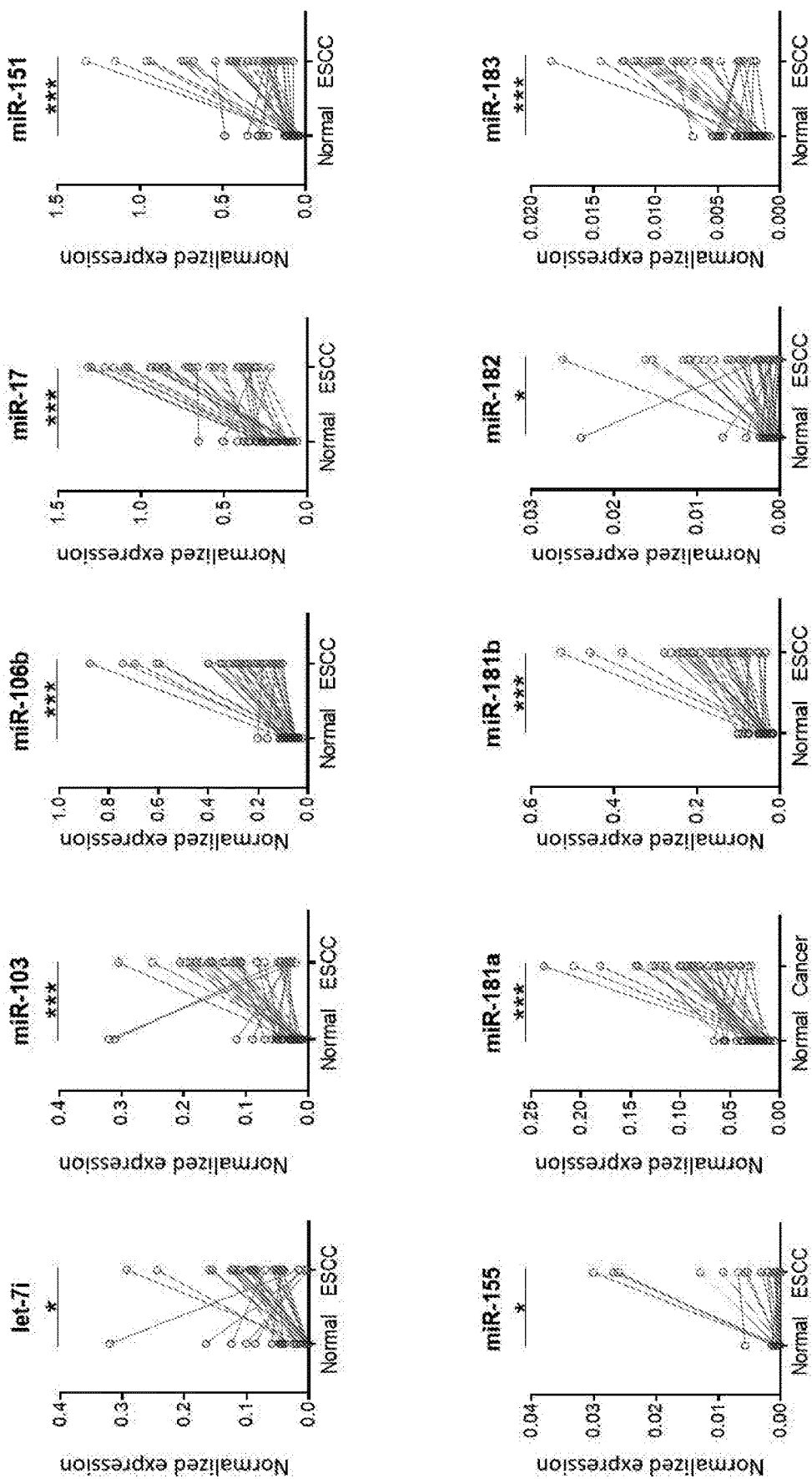
FIG. 17: Tissue validation for initial miRNA candidates. All of 18 in silico miRNA candidates were significantly upregulated in ESCC tissue samples compared with adjacent normal tissues by qRT-PCR on 32 ESCC and 32 matched adjacent normal tissues.
Figure 17:
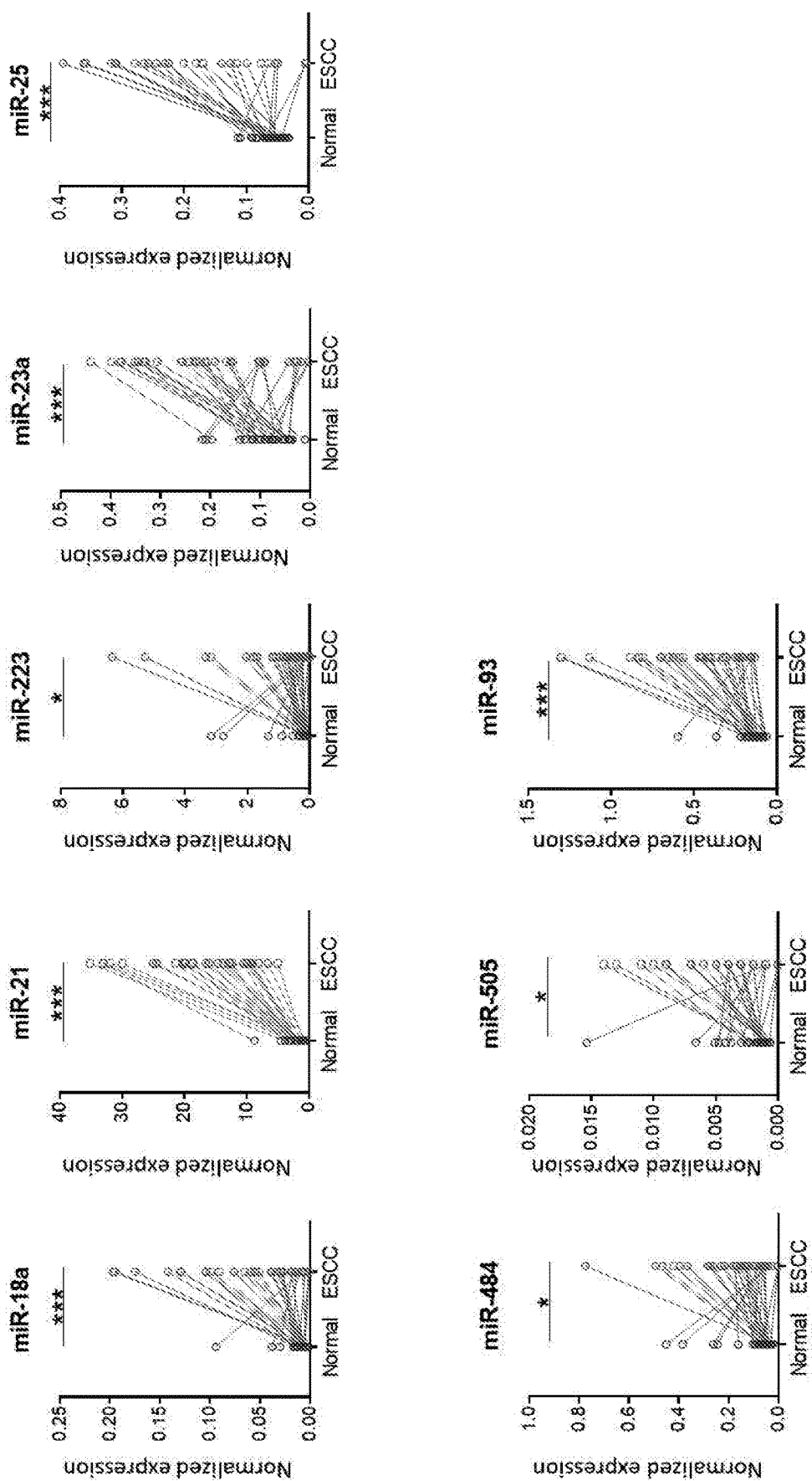

The flowchart in FIG. 16 illustrates the overall study design. In the discovery phase, the inventors interrogated three tissue-based miRNA expression datasets (TCGA, GSE55856, GSE43732) to prioritize miRNA panel candidates. For each dataset, a miRNA is considered as a potential candidate if it is: (1) differentially expressed between ESCC and normal samples (log 2 fold-change>0.5, FDR-adjusted p-value<0.05); (2) discriminative between ESCC and normal samples (AUC>0.7); (3) upregulated in ESCC and has a relatively high expression to facilitate detection in the clinic (average expression>median of average expression of all differentially expressed miRNAs). Consequently, 79, 431, and 136 miRNAs were identified from the TCGA, GSE55856 and GSE43732 dataset, respectively, among which 18 miRNAs overlapped between the three datasets were prioritized as the miRNA panel candidates (FIG. 13A). To evaluate the diagnostic value of the 18-miRNA panel, two different strategies were employed. (1) Within each cohort, multivariate logistic regression with 2-fold cross-validation (repeated for 100 times) demonstrated a robust diagnostic value (average AUC=0.98, 0.99, 0.98, respectively) (FIG. 13B). (2) A multivariate logistic regression model trained on GSE55856 also achieved high predictive performance on all three datasets (AUC=0.99, 1.00, 0.99, respectively) (Data not shown). Furthermore, the inventors performed qRT-PCR on 32 ESCC and 32 matched adjacent normal tissues, and confirmed that all the 18 miRNAs were significantly upregulated (p-value<0.05) in ESCC clinical tissue samples (FIG. 17).

3. Establish a Circulating miRNA Panel for Prediction of ESCC

Figure 14:
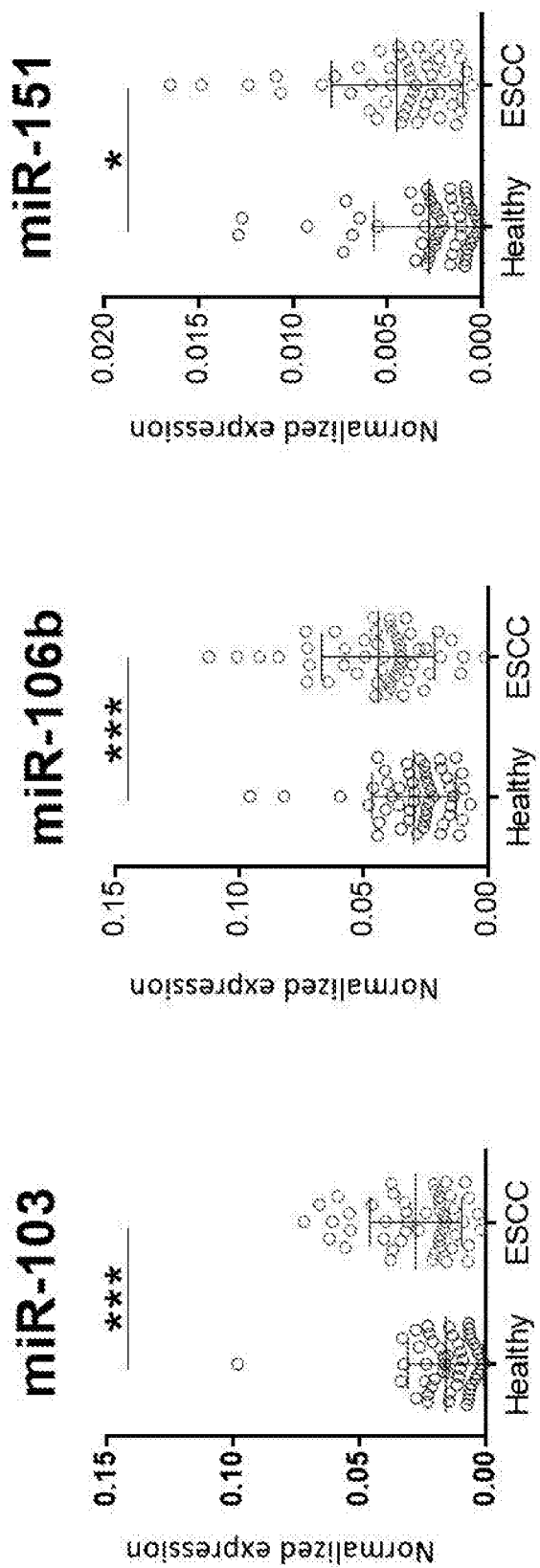
FIG. 14: Selection of candidate miRNAs in the serum testing cohort. Eight candidate miRNAs were significantly upregulated in ESCC serum for the serum testing cohort.
Figure 14:
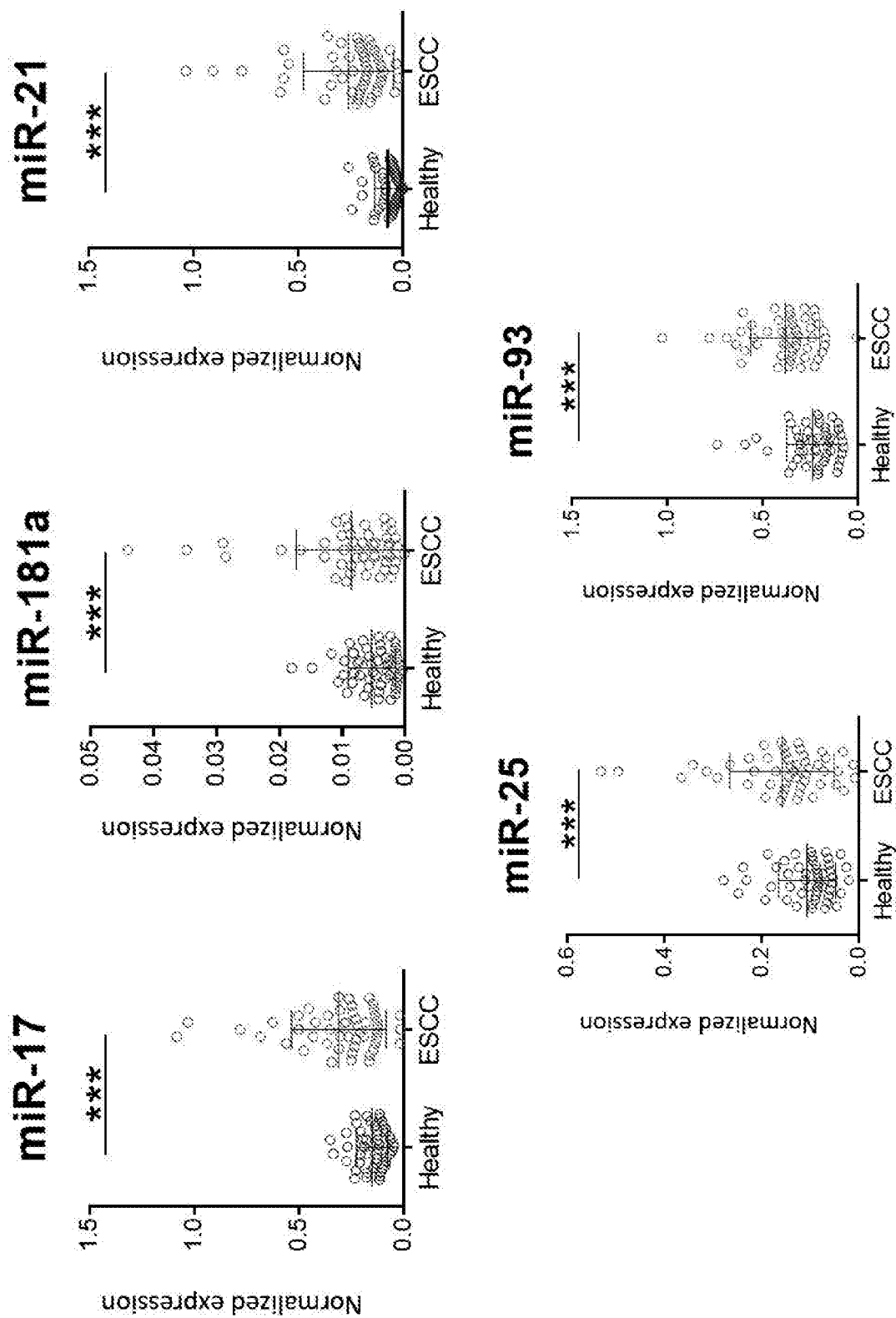

Using the serum refining cohort (50 ESCC, 50 healthy controls), the inventors next aimed to refine the 18 tissue-derived candidates to develop a circulating miRNA panel. Out of the total 18 candidates, 4 miRNAs (miR-182, miR-183, miR-18a, miR-505) below the detection limit (average Cycle threshold>35) were excluded. Among the other 14 detectable miRNAs, 8 (miR-103, miR-106b, miR-151, miR-17, miR-181a, miR-21, miR-25, miR-93) were significantly upregulated in ESCC serum (FIG. 14). The inventors subsequently performed qRT-PCR for the 8 miRNAs on the serum training cohort (208 ESCC, 128 healthy controls), and trained a multivariate logistic regression model. A risk scoring formula was derived from the multivariate model as follows: logit(P)=0.209*miR21+0.968*miR93+0.454*miR106b+3.753*miR17−8.505*miR181a+4.149*miR25−1.375*miR103−3.278*miR151−0.998. On the training cohort, the 8-miRNA model achieved an AUC of 0.83 (95% CI, 0.79-0.87), a sensitivity of 78%, and a specificity of 75% (FIG. 15A).

4. Diagnostic Performance of the Circulating miRNA Panel in Two Validation Cohorts To validate the diagnostic value of the 8-miRNA panel, the inventors performed qRT-PCR on two additional independent serum cohorts: serum validation cohort 1 (106 ESCC patients, 20 healthy controls) and serum validation cohort 2 (123 ESCC patients, 42 healthy controls). For each cohort, the inventors calculated risk scores using the 8-miRNA model and determined high- or low-risk groups using the corresponding cut-off value (0.582) derived from serum training cohort. The 8-miRNA model achieved a robust predictive performance on both serum validation cohort 1 (FIG. 15B, AUC: 0.80, 95% CI: 0.69-0.91, sensitivity: 89%, specificity: 60%) and serum validation cohort 2 (FIG. 15C, AUC: 0.89, 95% CI: 0.83-0.94, sensitivity: 87%, specificity: 85%). Importantly, while the conventional tumor marker of squamous cell carcinoma-related antigen (SCC-Ag) showed some value for ESCC diagnosis (AUC: 0.71, 95% CI: 0.60-0.84, sensitivity: 0.91, specificity: 0.69) on serum validation cohort 2 (123 stage I-IV ESCC patients VS 42 healthy controls), the 8-miRNA model demonstrated significantly higher diagnostic performance (p-value=0.003, DeLong's test). Especially, the 8-miRNA panel could distinguish stage I ESCC patients (n=20) from healthy controls (n=42) (AUC: 0.81, 95% CI: 0.70-0.94, sensitivity: 0.76, specificity: 0.91), which is superior (p-value=0.025, DeLong's test) to SCC-Ag (AUC=0.63, 95% CI: 0.50-0.78, sensitivity: 0.75, specificity: 0.69). These validation results demonstrated a promising potential to use the 8-miRNA model as a robust biomarker for non-invasive early detection of ESCC in the clinic.

C. Discussion

ESCC is one of the most aggressive cancers with poor prognosis, and low survival rate of the patients is largely due to delayed diagnosis. Therefore, early detection of ESCC provides opportunities to implement effective treatments and timely interventions to improve the patient outcomes. However, currently, there is no clinically viable molecular marker for ESCC diagnosis. In this study, the inventors utilized bioinformatic approaches to identify candidate miRNAs from three in silico datasets. The inventors then evaluated the expression of these miRNAs in serum and established a robust miRNA panel as a non-invasive diagnostic marker for ESCC and validated in three independent cohorts. Interestingly, even for early stage ESCC patients, the inventors showed that the miRNA panel had significantly better detection capability than SCC-Ag, the most commonly used serum diagnostic marker of ESCC. In conclusion, for the first time, using a comprehensive biomarker discovery process with three large independent validation cohorts, the inventors have developed and successfully validated a novel and robust miRNA-based panel for the early detection of ESCC, which has the potential for transforming noninvasive diagnostics of ESCC patients in future.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims. All references and publications referred to throughout the disclosure are incorporated by reference for all purposes.

The invention claimed is:

1. A method for treating a patient that has esophageal cancer comprising:
   measuring an elevated level of expression of a group of mature microRNA molecules in a biological sample from the patient relative to the expression level of the same group of mature microRNA molecules in a control biological sample, wherein the group consists of: miR-103, miR-106b, miR-151, miR-17, miR-181a, miR-21, miR-25, and miR-93, and
   administering an esophageal cancer treatment to the patient comprising chemotherapy, radiation therapy, surgery or a combination thereof.

2. The method of claim 1, wherein the method further comprises obtaining the biological sample from the patient.

3. The method of claim 1, wherein the control biological sample is a non-esophageal cancer patient sample.

4. The method of claim 1, wherein the control biological sample is a non-cancerous biological sample.

5. The method of claim 1, wherein the esophageal cancer is esophagus squamous-cell carcinoma (ESCC) or esophagus adenocarcinoma (EAC).

6. The method of claim 1, wherein the biological sample from the patient and the control biological sample are a tissue or serum sample.

7. The method of claim 1, wherein the biological sample from the patient is from a primary tumor.

8. The method of claim 1, wherein the esophageal cancer comprises lymph node metastasis.

9. The method of claim 1, wherein the esophageal cancer comprises distant metastasis.

* * * * *